US012584152B2

(12) United States Patent  (10) Patent No.: US 12,584,152 B2
Seo et al.  (45) Date of Patent: Mar. 24, 2026

(54) L-THREONINE EXPORT PROTEIN VARIANT AND METHOD FOR PRODUCTION OF L-THREONINE USING SAME

(71) Applicant: CJ CHEILJEDANG CORPORATION, Seoul (KR)

(72) Inventors: Chang Il Seo, Seoul (KR); Hyo Jin Kim, Seoul (KR); Ji Sun Lee, Seoul (KR); Sol Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 1051 days.

(21) Appl. No.: 17/623,226

(22) PCT Filed: Sep. 9, 2020

(86) PCT No.: PCT/KR2020/012154
§ 371 (c)(1),
(2) Date: Dec. 27, 2021

(87) PCT Pub. No.: WO2021/049866
PCT Pub. Date: Mar. 18, 2021

(65) Prior Publication Data
US 2023/0012923 A1     Jan. 19, 2023

(30) Foreign Application Priority Data

Sep. 9, 2019     (KR) ........................ 10-2019-0111509

(51) Int. Cl.
| *C12P 13/08* | (2006.01) |
| *C12N 1/20* | (2006.01) |
| *C12N 15/52* | (2006.01) |
| *C12N 15/70* | (2006.01) |

(52) U.S. Cl.
CPC ............... *C12P 13/08* (2013.01); *C12N 1/20* (2013.01); *C12N 15/52* (2013.01); *C12N 15/70* (2013.01); *C12Y 101/01003* (2013.01); *C12Y 207/02004* (2013.01); *C12N 2800/101* (2013.01)

(58) Field of Classification Search
None
See application file for complete search history.

(56) References Cited

U.S. PATENT DOCUMENTS

| 6,858,406 | B1 * | 2/2005 | Vrlijc | C07K 14/34 |
| | | | | 435/252.32 |
| 8,758,764 | B2 * | 6/2014 | Masignani | A61K 39/0258 |
| | | | | 424/257.1 |
| 9,394,346 | B2 * | 7/2016 | Livshits | C12P 13/08 |
| 2003/0017554 | A1 | 1/2003 | Rieping et al. | |

FOREIGN PATENT DOCUMENTS

| CN | 104845995 | A | 8/2015 |
| EP | 1016710 | B1 | 7/2000 |
| JP | 2005-227977 | A | 8/2005 |
| KR | 10-0159812 | B | 11/1998 |
| KR | 10-2000-0048340 | A | 7/2000 |
| KR | 10-0620092 | B | 9/2006 |
| KR | 10-2008-0082880 | A | 9/2008 |
| KR | 10-1783170 | B | 9/2017 |
| WO | WO 9723597 | A2 | 7/1997 |

OTHER PUBLICATIONS

Strategies to Optimize Protein Expression in *E. coli*, Francis et al (Year: 2010).*
The English translation of the International Search Report of PCT/US2020/012154 mailed Jan. 7, 2021.
NCBI, GenBank accession No. WP_097344017.1 "threonine export protein RhtC [*Escherichia coli*]", Jun. 20, 2019.
Daley DO et al., Global topology analysis of the *Escherichia coli* inner membrane proteome, Science. May 27, 2005; 308(5726):1321-3.
Office Action of Japanese Patent Application No. 2021-569881 dated Sep. 27, 2022; 7 pages.
Accession No. A0A3R0W092, Database UniProt [online], Apr. 10, 2019; hhttps://rest.uniprot.org/unisave/A0A3R0W092?format=txt&versions=1> Sep. 20, 2022.

* cited by examiner

*Primary Examiner* — Manjunath N Rao
(74) *Attorney, Agent, or Firm* — Squire Patton Boggs (US) LLP

(57) ABSTRACT

The present disclosure relates to an L-threonine export protein variant, a microorganism including same, and a method for production of L-threonine using same.

9 Claims, No Drawings

Specification includes a Sequence Listing.

SEQUENCE LISTING

<160> NUMBER OF SEQ ID NOS: 116

<210> SEQ ID NO 1
<211> LENGTH: 206
<212> TYPE: PRT
<213> ORGANISM: Unknown
<220> FEATURE:
<223> OTHER INFORMATION: rhtC wild type

<400> SEQUENCE: 1

```
Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Leu Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
                100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
    130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
            195                 200                 205
```

<210> SEQ ID NO 2

```
<211> LENGTH: 621
<212> TYPE: DNA
<213> ORGANISM: Unknown
<220> FEATURE:
<223> OTHER INFORMATION: rhtC wild type

<400> SEQUENCE: 2
atgttgatgt tatttctcac cgtcgccatg gtgcacattg tggcgcttat gagccccggt      60
cccgatttct tttttgtctc tcagaccgct gtcagtcgtt cccgtaaaga agcgatgatg     120
ggcgtgctgg gcattacctg cggcgtaatg gtttgggctg ggattgcgct gcttggcctg     180
catttgatta tcgaaaaaat ggcctggctg catacgctga ttatggtggg cggtggcctg     240
tatctctgct ggatgggtta ccagatgcta cgtggtgcac tgaaaaaaga ggcggtttct     300
gcacctgcgc cacaggtcga gctggcgaaa agtgggcgca gtttcctgaa aggtttactg     360
accaatctcg ctaatccgaa agcgattatc tactttggct cggtgttctc attgtttgtc     420
ggtgataacg ttggcactac cgcgcgctgg ggcattttg cgctgatcat tgtcgaaacg     480
ctggcgtggt ttaccgtcgt tgccagcctg tttgccctgc cgcaaatgcg ccgtggttat     540
caacgtctgg cgaagtggat tgatggtttt gccggggcgt tatttgccgg atttggcatt     600
catttgatta tttcgcggtg a                                               621

<210> SEQ ID NO 3
<211> LENGTH: 35
<212> TYPE: DNA
<213> ORGANISM: Artificial Sequence
<220> FEATURE:
<223> OTHER INFORMATION: Synthetic: lysC promoter Up 1

<400> SEQUENCE: 3
tcgagctcgg tacccgacag gacaagcact ggttg                                 35

<210> SEQ ID NO 4
<211> LENGTH: 35
<212> TYPE: DNA
<213> ORGANISM: Artificial Sequence
<220> FEATURE:
<223> OTHER INFORMATION: Synthetic: lysC promoter Up 2

<400> SEQUENCE: 4
agtagcgctg ggatgtttct ctttgtgcac ctttc                                 35

<210> SEQ ID NO 5
<211> LENGTH: 35
<212> TYPE: DNA
<213> ORGANISM: Artificial Sequence
<220> FEATURE:
<223> OTHER INFORMATION: Synthetic: Pcj7 1

<400> SEQUENCE: 5
gaaaggtgca caaagagaaa catcccagcg ctact                                 35

<210> SEQ ID NO 6
<211> LENGTH: 35
<212> TYPE: DNA
<213> ORGANISM: Artificial Sequence
<220> FEATURE:
<223> OTHER INFORMATION: Synthetic: Pcj7 2

<400> SEQUENCE: 6
tacgaccagg gccatgagtg tttcctttcg ttggg                                 35
```

-continued

```
<210> SEQ ID NO 7
<211> LENGTH: 35
<212> TYPE: DNA
<213> ORGANISM: Artificial Sequence
<220> FEATURE:
<223> OTHER INFORMATION: Synthetic: lysC 1

<400> SEQUENCE: 7
cgaaaggaaa cactcatggc cctggtcgta cagaa                                35

<210> SEQ ID NO 8
<211> LENGTH: 30
<212> TYPE: DNA
<213> ORGANISM: Artificial Sequence
<220> FEATURE:
<223> OTHER INFORMATION: Synthetic: lysC 2

<400> SEQUENCE: 8
ggtggaaatc ttttcgatgt tcacgttgac                                     30

<210> SEQ ID NO 9
<211> LENGTH: 30
<212> TYPE: DNA
<213> ORGANISM: Artificial Sequence
<220> FEATURE:
<223> OTHER INFORMATION: Synthetic: lysC Down 1

<400> SEQUENCE: 9
gaacatcgaa aagatttcca cctctgagat                                     30

<210> SEQ ID NO 10
<211> LENGTH: 35
<212> TYPE: DNA
<213> ORGANISM: Artificial Sequence
<220> FEATURE:
<223> OTHER INFORMATION: Synthetic: lysC Down 2

<400> SEQUENCE: 10
ctctagagga tccccgttca cctcagagac gatta                               35

<210> SEQ ID NO 11
<211> LENGTH: 20
<212> TYPE: DNA
<213> ORGANISM: Artificial Sequence
<220> FEATURE:
<223> OTHER INFORMATION: Synthetic: confirm lysC 1

<400> SEQUENCE: 11
acattccacc cattactgca                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic: confirm lysC 2

<400> SEQUENCE: 12
tcttcatcgg tttcgaaggt                                                20

<210> SEQ ID NO 13
<211> LENGTH: 30
<212> TYPE: DNA
<213> ORGANISM: Artificial Sequence
<220> FEATURE:
<223> OTHER INFORMATION: Synthetic: cj7 F
```

<400> SEQUENCE: 13
gaagctccaa agaaacatcc cagcgctact                                     30

<210> SEQ ID NO 14
<211> LENGTH: 35
<212> TYPE: DNA
<213> ORGANISM: Artificial Sequence
<220> FEATURE:
<223> OTHER INFORMATION: Synthetic: up F

<400> SEQUENCE: 14
tcgagctcgg taccctgtct ccgtatgcag tgagc                               35

<210> SEQ ID NO 15
<211> LENGTH: 22
<212> TYPE: DNA
<213> ORGANISM: Artificial Sequence
<220> FEATURE:
<223> OTHER INFORMATION: Synthetic: G378E F

<400> SEQUENCE: 15
aagatcgcgt ggaggttttg gc                                             22

<210> SEQ ID NO 16
<211> LENGTH: 35
<212> TYPE: DNA
<213> ORGANISM: Artificial Sequence
<220> FEATURE:
<223> OTHER INFORMATION: Synthetic: CJ7 R

<400> SEQUENCE: 16
tgtgtgagtc gacatgagtg tttcctttcg ttggg                               35

<210> SEQ ID NO 17
<211> LENGTH: 35
<212> TYPE: DNA
<213> ORGANISM: Artificial Sequence
<220> FEATURE:
<223> OTHER INFORMATION: Synthetic: hom F

<400> SEQUENCE: 17
tataggagaa caatcatgac ctcagcatct gcccc                               35

<210> SEQ ID NO 18
<211> LENGTH: 22
<212> TYPE: DNA
<213> ORGANISM: Artificial Sequence
<220> FEATURE:
<223> OTHER INFORMATION: Synthetic: G378E R

<400> SEQUENCE: 18
gccaaaacct ccacgcgatc tt                                             22

<210> SEQ ID NO 19
<211> LENGTH: 25
<212> TYPE: DNA
<213> ORGANISM: Artificial Sequence
<220> FEATURE:
<223> OTHER INFORMATION: Synthetic: R398Q F

<400> SEQUENCE: 19
gcgtacaatc caacaggaag agcgc                                          25

<210> SEQ ID NO 20
<211> LENGTH: 25

```
<212> TYPE: DNA
<213> ORGANISM: Artificial Sequence
<220> FEATURE:
<223> OTHER INFORMATION: Synthetic: R398Q F

<400> SEQUENCE: 20
gcgctcttcc tgttggattg tacgc                                          25

<210> SEQ ID NO 21
<211> LENGTH: 35
<212> TYPE: DNA
<213> ORGANISM: Artificial Sequence
<220> FEATURE:
<223> OTHER INFORMATION: Synthetic: hom R

<400> SEQUENCE: 21
ctctagagga tccccgactg cggaatgttg ttgtg                               35

<210> SEQ ID NO 22
<211> LENGTH: 20
<212> TYPE: DNA
<213> ORGANISM: Artificial Sequence
<220> FEATURE:
<223> OTHER INFORMATION: Synthetic: hom conf F

<400> SEQUENCE: 22
tgggtaggtc gagttgttaa                                                20

<210> SEQ ID NO 23
<211> LENGTH: 20
<212> TYPE: DNA
<213> ORGANISM: Artificial Sequence
<220> FEATURE:
<223> OTHER INFORMATION: Synthetic: hom conf R

<400> SEQUENCE: 23
cagcgcagtc gcacgaatat                                                20

<210> SEQ ID NO 24
<211> LENGTH: 40
<212> TYPE: DNA
<213> ORGANISM: Artificial Sequence
<220> FEATURE:
<223> OTHER INFORMATION: Synthetic: CJ7 F

<400> SEQUENCE: 24
caacctttgc aaggtgaaaa agaaacatcc cagcgctact                          40

<210> SEQ ID NO 25
<211> LENGTH: 35
<212> TYPE: DNA
<213> ORGANISM: Artificial Sequence
<220> FEATURE:
<223> OTHER INFORMATION: Synthetic: upstream F

<400> SEQUENCE: 25
tcgagctcgg taccctgaca gttgctgatc tggct                               35

<210> SEQ ID NO 26
<211> LENGTH: 40
<212> TYPE: DNA
<213> ORGANISM: Artificial Sequence
<220> FEATURE:
<223> OTHER INFORMATION: Synthetic: upstream R

<400> SEQUENCE: 26
```

-continued agtagcgctg ggatgtttct ttttcacctt gcaaaggttg                                    40

<210> SEQ ID NO 27
<211> LENGTH: 35
<212> TYPE: DNA
<213> ORGANISM: Artificial Sequence
<220> FEATURE:
<223> OTHER INFORMATION: Synthetic: pyc F

<400> SEQUENCE: 27
ggaataatta ctctaatgtc gactcacaca tcttc                                         35

<210> SEQ ID NO 28
<211> LENGTH: 35
<212> TYPE: DNA
<213> ORGANISM: Artificial Sequence
<220> FEATURE:
<223> OTHER INFORMATION: Synthetic: pyc R

<400> SEQUENCE: 28
ctctagagga tccccggcat tttcagacag gaagc                                         35

<210> SEQ ID NO 29
<211> LENGTH: 20
<212> TYPE: DNA
<213> ORGANISM: Artificial Sequence
<220> FEATURE:
<223> OTHER INFORMATION: Synthetic: pyc conf F

<400> SEQUENCE: 29
acgcactcgg tgaaggcgtg                                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic: pyc conf R

<400> SEQUENCE: 30
cgcttcagct tcacgagatg                                                          20

<210> SEQ ID NO 31
<211> LENGTH: 35
<212> TYPE: DNA
<213> ORGANISM: Artificial Sequence
<220> FEATURE:
<223> OTHER INFORMATION: Synthetic: Ncgl0179 UP F

<400> SEQUENCE: 31
tcgagctcgg tacccttttg agtaattggt aatac                                         35

<210> SEQ ID NO 32
<211> LENGTH: 34
<212> TYPE: DNA
<213> ORGANISM: Artificial Sequence
<220> FEATURE:
<223> OTHER INFORMATION: Synthetic: Ncgl0179 UP R

<400> SEQUENCE: 32
tgaagcgccg gtacccgctt aaacgggcga ttat                                          34

<210> SEQ ID NO 33
<211> LENGTH: 34
<212> TYPE: DNA
<213> ORGANISM: Artificial Sequence
<220> FEATURE:
<223> OTHER INFORMATION: Synthetic: SPL7 F

<400> SEQUENCE: 33
atcgcccgtt taagcgggta ccggcgcttc atgt                                    34

<210> SEQ ID NO 34
<211> LENGTH: 35
<212> TYPE: DNA
<213> ORGANISM: Artificial Sequence
<220> FEATURE:
<223> OTHER INFORMATION: Synthetic: SPL7 R

<400> SEQUENCE: 34
cttcaacact cgcatgatat ctgttttgat ctcct                                   35

<210> SEQ ID NO 35
<211> LENGTH: 35
<212> TYPE: DNA
<213> ORGANISM: Artificial Sequence
<220> FEATURE:
<223> OTHER INFORMATION: Synthetic: S352P UP F

<400> SEQUENCE: 35
atcaaaacag atatcatgcg agtgttgaag ttcgg                                   35

<210> SEQ ID NO 36
<211> LENGTH: 37
<212> TYPE: DNA
<213> ORGANISM: Artificial Sequence
<220> FEATURE:
<223> OTHER INFORMATION: Synthetic: S352P UP R

<400> SEQUENCE: 36
tactgtattc ggaagatggt tgcgtaatca gcaccac                                 37

<210> SEQ ID NO 37
<211> LENGTH: 35
<212> TYPE: DNA
<213> ORGANISM: Artificial Sequence
<220> FEATURE:
<223> OTHER INFORMATION: Synthetic: Ncgl0179 DOWN F

<400> SEQUENCE: 37
atgaatcatc agtaattaat ggccctcgat ttggc                                   35

<210> SEQ ID NO 38
<211> LENGTH: 34
<212> TYPE: DNA
<213> ORGANISM: Artificial Sequence
<220> FEATURE:
<223> OTHER INFORMATION: Synthetic: Ncgl0179 DOWN R

<400> SEQUENCE: 38
tctagaggat cccctggaat aatcagactc tgga                                    34

<210> SEQ ID NO 39
<211> LENGTH: 37
<212> TYPE: DNA
<213> ORGANISM: Artificial Sequence
<220> FEATURE:
<223> OTHER INFORMATION: Synthetic: S352P DOWN F

<400> SEQUENCE: 39
gtggtgctga ttacgcaacc atcttccgaa tacagta                                 37

-continued

```
<210> SEQ ID NO 40
<211> LENGTH: 36
<212> TYPE: DNA
<213> ORGANISM: Artificial Sequence
<220> FEATURE:
<223> OTHER INFORMATION: Synthetic: S352P DOWN R

<400> SEQUENCE: 40
aaatcgaggg ccattaatta ctgatgattc atcatc                               36

<210> SEQ ID NO 41
<211> LENGTH: 19
<212> TYPE: DNA
<213> ORGANISM: Artificial Sequence
<220> FEATURE:
<223> OTHER INFORMATION: Synthetic: thr conf F

<400> SEQUENCE: 41
gattcacatc accaatgtc                                                  19

<210> SEQ ID NO 42
<211> LENGTH: 19
<212> TYPE: DNA
<213> ORGANISM: Artificial Sequence
<220> FEATURE:
<223> OTHER INFORMATION: Synthetic: thr conf R

<400> SEQUENCE: 42
gacaccatcg cagcccgac                                                  19

<210> SEQ ID NO 43
<211> LENGTH: 40
<212> TYPE: DNA
<213> ORGANISM: Artificial Sequence
<220> FEATURE:
<223> OTHER INFORMATION: Synthetic: rhtC F

<400> SEQUENCE: 43
gtcgactcta gaggatcccc gctgattcgt gcgcatgttg                           40

<210> SEQ ID NO 44
<211> LENGTH: 40
<212> TYPE: DNA
<213> ORGANISM: Artificial Sequence
<220> FEATURE:
<223> OTHER INFORMATION: Synthetic: rhtC R

<400> SEQUENCE: 44
tgaattcgag ctcggtaccc tcaccgcgaa ataatcaaat                           40

<210> SEQ ID NO 45
<211> LENGTH: 35
<212> TYPE: DNA
<213> ORGANISM: Artificial Sequence
<220> FEATURE:
<223> OTHER INFORMATION: Synthetic: Ncgl2533 up F

<400> SEQUENCE: 45
tcgagctcgg taccccagca agatctagtc atcaa                                35

<210> SEQ ID NO 46
<211> LENGTH: 35
<212> TYPE: DNA
<213> ORGANISM: Artificial Sequence
<220> FEATURE:
<223> OTHER INFORMATION: Synthetic: Ncgl2533 up R
```

-continued

<400> SEQUENCE: 46
gtcgttttta ggcttccgct ggaaaacatt ttgca                          35

<210> SEQ ID NO 47
<211> LENGTH: 35
<212> TYPE: DNA
<213> ORGANISM: Artificial Sequence
<220> FEATURE:
<223> OTHER INFORMATION: Synthetic: PgapA F

<400> SEQUENCE: 47
aatgttttcc agcggaagcc taaaaacgac cgagc                          35

<210> SEQ ID NO 48
<211> LENGTH: 35
<212> TYPE: DNA
<213> ORGANISM: Artificial Sequence
<220> FEATURE:
<223> OTHER INFORMATION: Synthetic: PgapA R

<400> SEQUENCE: 48
aaataacatc aacatgttgt gtctcctcta aagat                          35

<210> SEQ ID NO 49
<211> LENGTH: 35
<212> TYPE: DNA
<213> ORGANISM: Artificial Sequence
<220> FEATURE:
<223> OTHER INFORMATION: Synthetic: rhtC_m F

<400> SEQUENCE: 49
tagaggagac acaacatgtt gatgttattt ctcac                          35

<210> SEQ ID NO 50
<211> LENGTH: 35
<212> TYPE: DNA
<213> ORGANISM: Artificial Sequence
<220> FEATURE:
<223> OTHER INFORMATION: Synthetic: rhtC_m R

<400> SEQUENCE: 50
taagcaggtt gattttcacc gcgaaataat caaat                          35

<210> SEQ ID NO 51
<211> LENGTH: 35
<212> TYPE: DNA
<213> ORGANISM: Artificial Sequence
<220> FEATURE:
<223> OTHER INFORMATION: Synthetic: Ncgl2533 dn F

<400> SEQUENCE: 51
attatttcgc ggtgaaaatc aacctgctta ggcgt                          35

<210> SEQ ID NO 52
<211> LENGTH: 35
<212> TYPE: DNA
<213> ORGANISM: Artificial Sequence
<220> FEATURE:
<223> OTHER INFORMATION: Synthetic: Ncgl2533 dn R

<400> SEQUENCE: 52
ctctagagga tcccctatag ctaccatctg ggtgg                          35

<210> SEQ ID NO 53

-continued

```
<211> LENGTH: 20
<212> TYPE: DNA
<213> ORGANISM: Artificial Sequence
<220> FEATURE:
<223> OTHER INFORMATION: Synthetic: HR outside F

<400> SEQUENCE: 53
aaggaatatc ccggagaacc                                            20

<210> SEQ ID NO 54
<211> LENGTH: 20
<212> TYPE: DNA
<213> ORGANISM: Artificial Sequence
<220> FEATURE:
<223> OTHER INFORMATION: Synthetic: HR outside R

<400> SEQUENCE: 54
ttgcgtttga aaagccctcg                                            20

<210> SEQ ID NO 55
<211> LENGTH: 30
<212> TYPE: DNA
<213> ORGANISM: Artificial Sequence
<220> FEATURE:
<223> OTHER INFORMATION: Synthetic: up R

<400> SEQUENCE: 55
ggatgtttct ttggagcttc gctcaatcat                                 30

<210> SEQ ID NO 56
<211> LENGTH: 35
<212> TYPE: DNA
<213> ORGANISM: Artificial Sequence
<220> FEATURE:
<223> OTHER INFORMATION: Synthetic: cj7 R

<400> SEQUENCE: 56
agatgctgag gtcatgattg ttctcctata atcgc                           35

<210> SEQ ID NO 57
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62R F

<400> SEQUENCE: 57
gcgctgcttg gcctgcatcg tattatcgaa aaaatggcc                       39

<210> SEQ ID NO 58
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62R R

<400> SEQUENCE: 58
ggccattttt tcgataatac gatgcaggcc aagcagcgc                       39

<210> SEQ ID NO 59
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62A F

<400> SEQUENCE: 59
```
gcgctgcttg gcctgcatgc gattatcgaa aaaatggcc 39

```
<210> SEQ ID NO 60
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62A R

<400> SEQUENCE: 60
```
ggccattttt tcgataatcg catgcaggcc aagcagcgc 39

```
<210> SEQ ID NO 61
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62D F

<400> SEQUENCE: 61
```
gcgctgcttg gcctgcatga cattatcgaa aaaatggcc 39

```
<210> SEQ ID NO 62
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62D R

<400> SEQUENCE: 62
```
ggccattttt tcgataatgt catgcaggcc aagcagcgc 39

```
<210> SEQ ID NO 63
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62K F

<400> SEQUENCE: 63
```
gcgctgcttg gcctgcataa aattatcgaa aaaatggcc 39

```
<210> SEQ ID NO 64
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62K R

<400> SEQUENCE: 64
```
ggccattttt tcgataattt tatgcaggcc aagcagcgc 39

```
<210> SEQ ID NO 65
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62P F

<400> SEQUENCE: 65
```
gcgctgcttg gcctgcatcc gattatcgaa aaaatggcc 39

```
<210> SEQ ID NO 66
<211> LENGTH: 39
<212> TYPE: DNA
```

-continued

<213> ORGANISM: Artificial Sequence
<220> FEATURE:
<223> OTHER INFORMATION: Synthetic: pDZ-PgapA_rhtC L62P R

<400> SEQUENCE: 66
ggccattttt tcgataatcg gatgcaggcc aagcagcgc                                  39

<210> SEQ ID NO 67
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62C F

<400> SEQUENCE: 67
gcgctgcttg gcctgcattg cattatcgaa aaaatggcc                                  39

<210> SEQ ID NO 68
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62C R

<400> SEQUENCE: 68
ggccattttt tcgataatgc aatgcaggcc aagcagcgc                                  39

<210> SEQ ID NO 69
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62G F

<400> SEQUENCE: 69
gcgctgcttg gcctgcatgg cattatcgaa aaaatggcc                                  39

<210> SEQ ID NO 70
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62G R

<400> SEQUENCE: 70
ggccattttt tcgataatgc catgcaggcc aagcagcgc                                  39

<210> SEQ ID NO 71
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62T F

<400> SEQUENCE: 71
gcgctgcttg gcctgcatac gattatcgaa aaaatggcc                                  39

<210> SEQ ID NO 72
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62T R

<400> SEQUENCE: 72
ggccattttt tcgataatcg tatgcaggcc aagcagcgc                                  39

-continued

```
<210> SEQ ID NO 73
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62I F

<400> SEQUENCE: 73
gcgctgcttg gcctgcatat tattatcgaa aaaatggcc                          39

<210> SEQ ID NO 74
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62I R

<400> SEQUENCE: 74
ggccattttt tcgataataa tatgcaggcc aagcagcgc                          39

<210> SEQ ID NO 75
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62Y F

<400> SEQUENCE: 75
gcgctgcttg gcctgcatta tattatcgaa aaaatggcc                          39

<210> SEQ ID NO 76
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62Y R

<400> SEQUENCE: 76
ggccattttt tcgataatat aatgcaggcc aagcagcgc                          39

<210> SEQ ID NO 77
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62V F

<400> SEQUENCE: 77
gcgctgcttg gcctgcatgt gattatcgaa aaaatggcc                          39

<210> SEQ ID NO 78
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62V R

<400> SEQUENCE: 78
ggccattttt tcgataatca catgcaggcc aagcagcgc                          39

<210> SEQ ID NO 79
<211> LENGTH: 39
<212> TYPE: DNA
<213> ORGANISM: Artificial Sequence
<220> FEATURE:
```

-continued

<223> OTHER INFORMATION: Synthetic: pDZ-PgapA_rhtC L62H F

<400> SEQUENCE: 79
gcgctgcttg gcctgcatca tattatcgaa aaaatggcc                              39

<210> SEQ ID NO 80
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62H R

<400> SEQUENCE: 80
ggccattttt tcgataatat gatgcaggcc aagcagcgc                              39

<210> SEQ ID NO 81
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62F F

<400> SEQUENCE: 81
gcgctgcttg gcctgcattt cattatcgaa aaaatggcc                              39

<210> SEQ ID NO 82
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62F R

<400> SEQUENCE: 82
ggccattttt tcgataatga aatgcaggcc aagcagcgc                              39

<210> SEQ ID NO 83
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62M F

<400> SEQUENCE: 83
gcgctgcttg gcctgcatat gattatcgaa aaaatggcc                              39

<210> SEQ ID NO 84
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62M R

<400> SEQUENCE: 84
ggccattttt tcgataatca tatgcaggcc aagcagcgc                              39

<210> SEQ ID NO 85
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62Q F

<400> SEQUENCE: 85
gcgctgcttg gcctgcatca gattatcgaa aaaatggcc                              39

```
<210> SEQ ID NO 86
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62Q R

<400> SEQUENCE: 86
ggccattttt tcgataatct gatgcaggcc aagcagcgc                         39

<210> SEQ ID NO 87
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62N F

<400> SEQUENCE: 87
gcgctgcttg gcctgcataa cattatcgaa aaaatggcc                         39

<210> SEQ ID NO 88
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62N R

<400> SEQUENCE: 88
ggccattttt tcgataatgt tatgcaggcc aagcagcgc                         39

<210> SEQ ID NO 89
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62E F

<400> SEQUENCE: 89
gcgctgcttg gcctgcatga aattatcgaa aaaatggcc                         39

<210> SEQ ID NO 90
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62E R

<400> SEQUENCE: 90
ggccattttt tcgataattt catgcaggcc aagcagcgc                         39

<210> SEQ ID NO 91
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62W F

<400> SEQUENCE: 91
gcgctgcttg gcctgcattg gattatcgaa aaaatggcc                         39

<210> SEQ ID NO 92
<211> LENGTH: 39
<212> TYPE: DNA
<213> ORGANISM: Artificial Sequence
<220> FEATURE:
<223> OTHER INFORMATION: Synthetic: pDZ-PgapA_rhtC L62W R
```

-continued

```
<400> SEQUENCE: 92
ggccattttt tcgataatcc aatgcaggcc aagcagcgc                              39

<210> SEQ ID NO 93
<211> LENGTH: 206
<212> TYPE: PRT
<213> ORGANISM: Artificial Sequence
<220> FEATURE:
<223> OTHER INFORMATION: Synthetic: rhtC A53T

<400> SEQUENCE: 93

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Thr Gly Ile Ala Leu Leu Gly Leu His Leu Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 94
<211> LENGTH: 206
<212> TYPE: PRT
<213> ORGANISM: Artificial Sequence
<220> FEATURE:
<223> OTHER INFORMATION: Synthetic: rhtC L62S

<400> SEQUENCE: 94

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Ser Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
```

```
                    85                  90                  95
Glu Ala Val Ser Ala Pro Ala Pro Gln Val Glu Leu Ala Lys Ser Gly
                100                 105                 110
Arg Ser Phe Leu Lys Gly Leu Leu Thr Asn Leu Ala Asn Pro Lys Ala
            115                 120                 125
Ile Ile Tyr Phe Gly Ser Val Phe Ser Leu Phe Val Gly Asp Asn Val
            130                 135                 140
Gly Thr Thr Ala Arg Trp Gly Ile Phe Ala Leu Ile Ile Val Glu Thr
145                 150                 155                 160
Leu Ala Trp Phe Thr Val Val Ala Ser Leu Phe Ala Leu Pro Gln Met
                165                 170                 175
Arg Arg Gly Tyr Gln Arg Leu Ala Lys Trp Ile Asp Gly Phe Ala Gly
                180                 185                 190
Ala Leu Phe Ala Gly Phe Gly Ile His Leu Ile Ile Ser Arg
                195                 200                 205
```

<210> SEQ ID NO 95
<211> LENGTH: 206
<212> TYPE: PRT
<213> ORGANISM: Artificial Sequence
<220> FEATURE:
<223> OTHER INFORMATION: Synthetic: rhtC L62R

<400> SEQUENCE: 95

```
Met Leu Met Leu Phe Leu Thr Val Ala Met Val His Ile Val Ala Leu
1               5                   10                  15
Met Ser Pro Gly Pro Asp Phe Phe Phe Val Ser Gln Thr Ala Val Ser
                20                  25                  30
Arg Ser Arg Lys Glu Ala Met Met Gly Val Leu Gly Ile Thr Cys Gly
            35                  40                  45
Val Met Val Trp Ala Gly Ile Ala Leu Leu Gly Leu His Arg Ile Ile
        50                  55                  60
Glu Lys Met Ala Trp Leu His Thr Leu Ile Met Val Gly Gly Gly Leu
65                  70                  75                  80
Tyr Leu Cys Trp Met Gly Tyr Gln Met Leu Arg Gly Ala Leu Lys Lys
                85                  90                  95
Glu Ala Val Ser Ala Pro Ala Pro Gln Val Glu Leu Ala Lys Ser Gly
                100                 105                 110
Arg Ser Phe Leu Lys Gly Leu Leu Thr Asn Leu Ala Asn Pro Lys Ala
            115                 120                 125
Ile Ile Tyr Phe Gly Ser Val Phe Ser Leu Phe Val Gly Asp Asn Val
            130                 135                 140
Gly Thr Thr Ala Arg Trp Gly Ile Phe Ala Leu Ile Ile Val Glu Thr
145                 150                 155                 160
Leu Ala Trp Phe Thr Val Val Ala Ser Leu Phe Ala Leu Pro Gln Met
                165                 170                 175
Arg Arg Gly Tyr Gln Arg Leu Ala Lys Trp Ile Asp Gly Phe Ala Gly
                180                 185                 190
Ala Leu Phe Ala Gly Phe Gly Ile His Leu Ile Ile Ser Arg
                195                 200                 205
```

<210> SEQ ID NO 96
<211> LENGTH: 206
<212> TYPE: PRT
<213> ORGANISM: Artificial Sequence
<220> FEATURE:
<223> OTHER INFORMATION: Synthetic: rhtC L62A

<400> SEQUENCE: 96

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Ala Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
    130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 97
<211> LENGTH: 206
<212> TYPE: PRT
<213> ORGANISM: Artificial Sequence
<220> FEATURE:
<223> OTHER INFORMATION: Synthetic: rhtC L62D

<400> SEQUENCE: 97

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Asp Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
    130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 98
<211> LENGTH: 206
<212> TYPE: PRT
<213> ORGANISM: Artificial Sequence
<220> FEATURE:
<223> OTHER INFORMATION: Synthetic: rhtC L62K

<400> SEQUENCE: 98

Met Leu Met Leu Phe Leu Thr Val Ala Met Val His Ile Val Ala Leu
1                   5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Lys Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 99
<211> LENGTH: 206
<212> TYPE: PRT
<213> ORGANISM: Artificial Sequence
<220> FEATURE:
<223> OTHER INFORMATION: Synthetic: rhtC L62P

<400> SEQUENCE: 99

Met Leu Met Leu Phe Leu Thr Val Ala Met Val His Ile Val Ala Leu
1                   5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

```
Val Met Val Trp Ala Gly Ile Ala Leu Leu Gly Leu His Pro Ile Ile
    50              55              60

Glu Lys Met Ala Trp Leu His Thr Leu Ile Met Val Gly Gly Gly Leu
65              70              75              80

Tyr Leu Cys Trp Met Gly Tyr Gln Met Leu Arg Gly Ala Leu Lys Lys
            85              90              95

Glu Ala Val Ser Ala Pro Ala Pro Gln Val Glu Leu Ala Lys Ser Gly
            100             105             110

Arg Ser Phe Leu Lys Gly Leu Leu Thr Asn Leu Ala Asn Pro Lys Ala
            115             120             125

Ile Ile Tyr Phe Gly Ser Val Phe Ser Leu Phe Val Gly Asp Asn Val
            130             135             140

Gly Thr Thr Ala Arg Trp Gly Ile Phe Ala Leu Ile Ile Val Glu Thr
145             150             155             160

Leu Ala Trp Phe Thr Val Val Ala Ser Leu Phe Ala Leu Pro Gln Met
                165             170             175

Arg Arg Gly Tyr Gln Arg Leu Ala Lys Trp Ile Asp Gly Phe Ala Gly
                180             185             190

Ala Leu Phe Ala Gly Phe Gly Ile His Leu Ile Ile Ser Arg
            195             200             205
```

```
<210> SEQ ID NO 100
<211> LENGTH: 206
<212> TYPE: PRT
<213> ORGANISM: Artificial Sequence
<220> FEATURE:
<223> OTHER INFORMATION: Synthetic: rhtC L62C

<400> SEQUENCE: 100

Met Leu Met Leu Phe Leu Thr Val Ala Met Val His Ile Val Ala Leu
1               5               10              15

Met Ser Pro Gly Pro Asp Phe Phe Phe Val Ser Gln Thr Ala Val Ser
            20              25              30

Arg Ser Arg Lys Glu Ala Met Met Gly Val Leu Gly Ile Thr Cys Gly
        35              40              45

Val Met Val Trp Ala Gly Ile Ala Leu Leu Gly Leu His Cys Ile Ile
    50              55              60

Glu Lys Met Ala Trp Leu His Thr Leu Ile Met Val Gly Gly Gly Leu
65              70              75              80

Tyr Leu Cys Trp Met Gly Tyr Gln Met Leu Arg Gly Ala Leu Lys Lys
            85              90              95

Glu Ala Val Ser Ala Pro Ala Pro Gln Val Glu Leu Ala Lys Ser Gly
            100             105             110

Arg Ser Phe Leu Lys Gly Leu Leu Thr Asn Leu Ala Asn Pro Lys Ala
            115             120             125

Ile Ile Tyr Phe Gly Ser Val Phe Ser Leu Phe Val Gly Asp Asn Val
            130             135             140

Gly Thr Thr Ala Arg Trp Gly Ile Phe Ala Leu Ile Ile Val Glu Thr
145             150             155             160

Leu Ala Trp Phe Thr Val Val Ala Ser Leu Phe Ala Leu Pro Gln Met
                165             170             175

Arg Arg Gly Tyr Gln Arg Leu Ala Lys Trp Ile Asp Gly Phe Ala Gly
                180             185             190

Ala Leu Phe Ala Gly Phe Gly Ile His Leu Ile Ile Ser Arg
            195             200             205
```

```
<210> SEQ ID NO 101
<211> LENGTH: 206
<212> TYPE: PRT
<213> ORGANISM: Artificial Sequence
<220> FEATURE:
<223> OTHER INFORMATION: Synthetic: rhtC L62G

<400> SEQUENCE: 101

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Gly Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
                100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
                180                 185                 190

Ala Leu Phe Ala Gly Phe Gly Ile His Leu Ile Ile Ser Arg
            195                 200                 205

<210> SEQ ID NO 102
<211> LENGTH: 206
<212> TYPE: PRT
<213> ORGANISM: Artificial Sequence
<220> FEATURE:
<223> OTHER INFORMATION: Synthetic: rhtC L62T

<400> SEQUENCE: 102

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Thr Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
```

-continued

```
                100                 105                 110
Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
                180                 185                 190

Ala Leu Phe Ala Gly Phe Gly Ile His Leu Ile Ile Ser Arg
                195                 200                 205

<210> SEQ ID NO 103
<211> LENGTH: 206
<212> TYPE: PRT
<213> ORGANISM: Artificial Sequence
<220> FEATURE:
<223> OTHER INFORMATION: Synthetic: rhtC L62I

<400> SEQUENCE: 103

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Ile Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
                100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
                180                 185                 190

Ala Leu Phe Ala Gly Phe Gly Ile His Leu Ile Ile Ser Arg
                195                 200                 205

<210> SEQ ID NO 104
<211> LENGTH: 206
<212> TYPE: PRT
<213> ORGANISM: Artificial Sequence
<220> FEATURE:
<223> OTHER INFORMATION: Synthetic: rhtC L62Y

<400> SEQUENCE: 104
```

```
Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Tyr Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
            195                 200                 205
```

<210> SEQ ID NO 105
<211> LENGTH: 206
<212> TYPE: PRT
<213> ORGANISM: Artificial Sequence
<220> FEATURE:
<223> OTHER INFORMATION: Synthetic: rhtC L62V

<400> SEQUENCE: 105

```
Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Val Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160
```

Leu Ala Trp Phe Thr Val Val Ala Ser Leu Phe Ala Leu Pro Gln Met
                    165                 170                 175

Arg Arg Gly Tyr Gln Arg Leu Ala Lys Trp Ile Asp Gly Phe Ala Gly
                180                 185                 190

Ala Leu Phe Ala Gly Phe Gly Ile His Leu Ile Ile Ser Arg
            195                 200                 205

<210> SEQ ID NO 106
<211> LENGTH: 206
<212> TYPE: PRT
<213> ORGANISM: Artificial Sequence
<220> FEATURE:
<223> OTHER INFORMATION: Synthetic: rhtC L62H

<400> SEQUENCE: 106

Met Leu Met Leu Phe Leu Thr Val Ala Met Val His Ile Val Ala Leu
1                   5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His His Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                    165                 170                 175

Arg Arg Gly Tyr Gln Arg Leu Ala Lys Trp Ile Asp Gly Phe Ala Gly
                180                 185                 190

Ala Leu Phe Ala Gly Phe Gly Ile His Leu Ile Ile Ser Arg
            195                 200                 205

<210> SEQ ID NO 107
<211> LENGTH: 206
<212> TYPE: PRT
<213> ORGANISM: Artificial Sequence
<220> FEATURE:
<223> OTHER INFORMATION: Synthetic: rhtC L62F

<400> SEQUENCE: 107

Met Leu Met Leu Phe Leu Thr Val Ala Met Val His Ile Val Ala Leu
1                   5                   10                  15

Met Ser Pro Gly Pro Asp Phe Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Phe Ile Ile
        50                  55                  60

-continued

```
Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
            195                 200                 205
```

```
<210> SEQ ID NO 108
<211> LENGTH: 206
<212> TYPE: PRT
<213> ORGANISM: Artificial Sequence
<220> FEATURE:
<223> OTHER INFORMATION: Synthetic: rhtC L62M
```

<400> SEQUENCE: 108

```
Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Met Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
            115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
            195                 200                 205
```

<210> SEQ ID NO 109

```
<211> LENGTH: 206
<212> TYPE: PRT
<213> ORGANISM: Artificial Sequence
<220> FEATURE:
<223> OTHER INFORMATION: Synthetic: rhtC L62Q

<400> SEQUENCE: 109

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Gln Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
        130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
            195                 200                 205

<210> SEQ ID NO 110
<211> LENGTH: 206
<212> TYPE: PRT
<213> ORGANISM: Artificial Sequence
<220> FEATURE:
<223> OTHER INFORMATION: Synthetic: rhtC L62N

<400> SEQUENCE: 110

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Asn Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
```

```
                115             120             125

Ile Ile Tyr Phe Gly Ser Val Phe Ser Leu Phe Val Gly Asp Asn Val
        130             135             140

Gly Thr Thr Ala Arg Trp Gly Ile Phe Ala Leu Ile Ile Val Glu Thr
145             150             155             160

Leu Ala Trp Phe Thr Val Val Ala Ser Leu Phe Ala Leu Pro Gln Met
                165             170             175

Arg Arg Gly Tyr Gln Arg Leu Ala Lys Trp Ile Asp Gly Phe Ala Gly
            180             185             190

Ala Leu Phe Ala Gly Phe Gly Ile His Leu Ile Ile Ser Arg
            195             200             205

<210> SEQ ID NO 111
<211> LENGTH: 206
<212> TYPE: PRT
<213> ORGANISM: Artificial Sequence
<220> FEATURE:
<223> OTHER INFORMATION: Synthetic: rhtC L62E

<400> SEQUENCE: 111

Met Leu Met Leu Phe Leu Thr Val Ala Met Val His Ile Val Ala Leu
1               5               10              15

Met Ser Pro Gly Pro Asp Phe Phe Phe Val Ser Gln Thr Ala Val Ser
            20              25              30

Arg Ser Arg Lys Glu Ala Met Met Gly Val Leu Gly Ile Thr Cys Gly
        35              40              45

Val Met Val Trp Ala Gly Ile Ala Leu Leu Gly Leu His Glu Ile Ile
    50              55              60

Glu Lys Met Ala Trp Leu His Thr Leu Ile Met Val Gly Gly Gly Leu
65              70              75              80

Tyr Leu Cys Trp Met Gly Tyr Gln Met Leu Arg Gly Ala Leu Lys Lys
                85              90              95

Glu Ala Val Ser Ala Pro Ala Pro Gln Val Glu Leu Ala Lys Ser Gly
            100             105             110

Arg Ser Phe Leu Lys Gly Leu Leu Thr Asn Leu Ala Asn Pro Lys Ala
            115             120             125

Ile Ile Tyr Phe Gly Ser Val Phe Ser Leu Phe Val Gly Asp Asn Val
        130             135             140

Gly Thr Thr Ala Arg Trp Gly Ile Phe Ala Leu Ile Ile Val Glu Thr
145             150             155             160

Leu Ala Trp Phe Thr Val Val Ala Ser Leu Phe Ala Leu Pro Gln Met
                165             170             175

Arg Arg Gly Tyr Gln Arg Leu Ala Lys Trp Ile Asp Gly Phe Ala Gly
            180             185             190

Ala Leu Phe Ala Gly Phe Gly Ile His Leu Ile Ile Ser Arg
            195             200             205

<210> SEQ ID NO 112
<211> LENGTH: 206
<212> TYPE: PRT
<213> ORGANISM: Artificial Sequence
<220> FEATURE:
<223> OTHER INFORMATION: Synthetic: rhtC L62W

<400> SEQUENCE: 112

Met Leu Met Leu Phe Leu Thr Val Ala Met Val His Ile Val Ala Leu
1               5               10              15
```

-continued

```
Met Ser Pro Gly Pro Asp Phe Phe Phe Val Ser Gln Thr Ala Val Ser
        20              25                  30

Arg Ser Arg Lys Glu Ala Met Met Gly Val Leu Gly Ile Thr Cys Gly
        35              40                  45

Val Met Val Trp Ala Gly Ile Ala Leu Leu Gly Leu His Trp Ile Ile
    50              55                  60

Glu Lys Met Ala Trp Leu His Thr Leu Ile Met Val Gly Gly Gly Leu
65                  70              75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100             105                 110

Arg Ser Phe Leu Lys Gly Leu Leu Thr Asn Leu Ala Asn Pro Lys Ala
            115             120                 125

Ile Ile Tyr Phe Gly Ser Val Phe Ser Leu Phe Val Gly Asp Asn Val
        130             135                 140

Gly Thr Thr Ala Arg Trp Gly Ile Phe Ala Leu Ile Ile Val Glu Thr
145                 150             155                 160

Leu Ala Trp Phe Thr Val Val Ala Ser Leu Phe Ala Leu Pro Gln Met
                165             170                 175

Arg Arg Gly Tyr Gln Arg Leu Ala Lys Trp Ile Asp Gly Phe Ala Gly
                180             185                 190

Ala Leu Phe Ala Gly Phe Gly Ile His Leu Ile Ile Ser Arg
                195             200                 205

<210> SEQ ID NO 113
<211> LENGTH: 206
<212> TYPE: PRT
<213> ORGANISM: Unknown
<220> FEATURE:
<223> OTHER INFORMATION: Shegella flexneri rhtC(sfe rhtC)

<400> SEQUENCE: 113

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
        20              25                  30

Arg Ser Arg Lys Glu Ala Met Met Gly Val Leu Gly Ile Thr Cys Gly
        35              40                  45

Val Met Val Trp Ala Gly Ile Ala Leu Leu Gly Leu His Leu Ile Ile
    50              55                  60

Glu Lys Met Ala Trp Leu His Thr Leu Ile Met Val Gly Gly Gly Leu
65                  70              75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100             105                 110

Arg Ser Phe Leu Lys Gly Leu Leu Thr Asn Leu Ala Asn Pro Lys Ala
            115             120                 125

Ile Ile Tyr Phe Gly Ser Val Phe Ser Leu Phe Val Gly Asp Asn Val
        130             135                 140

Gly Thr Thr Glu Arg Trp Gly Ile Phe Ala Leu Ile Ile Val Glu Thr
145                 150             155                 160

Leu Ala Trp Phe Thr Val Val Ala Ser Leu Phe Ala Leu Pro Gln Met
                165             170                 175
```

-continued

```
Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 114
<211> LENGTH: 206
<212> TYPE: PRT
<213> ORGANISM: Artificial Sequence
<220> FEATURE:
<223> OTHER INFORMATION: Synthetic: sfe rhtC L62S

<400> SEQUENCE: 114

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Ser Ile Ile
    50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
        130                 135                 140

Gly Thr Thr Glu Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 115
<211> LENGTH: 206
<212> TYPE: PRT
<213> ORGANISM: Unknown
<220> FEATURE:
<223> OTHER INFORMATION: Escherichia fergusonii rhtC(efe rhtC)

<400> SEQUENCE: 115

Met Leu Met Leu Phe Leu Thr Val Ala Met Val His Ile Val Ala Leu
1               5                   10                  15

Met Ser Pro Gly Pro Asp Phe Phe Phe Val Ser Gln Thr Ala Val Ser
            20                  25                  30

Arg Ser Arg Lys Glu Ala Met Met Gly Val Leu Gly Ile Thr Cys Gly
        35                  40                  45

Val Met Val Trp Ala Gly Ile Ala Leu Leu Gly Leu His Leu Ile Ile
    50                  55                  60

Glu Lys Met Ala Trp Leu His Thr Leu Ile Met Val Gly Gly Gly Leu
65                  70                  75                  80
```

-continued

```
Tyr Leu Cys Trp Met Gly Tyr Gln Met Leu Arg Gly Ala Leu Lys Lys
                85              90              95

Glu Ala Val Ser Ala Pro Ala Pro Gln Val Glu Leu Ala Lys Ser Gly
            100             105             110

Arg Ser Phe Leu Lys Gly Leu Leu Thr Asn Leu Ala Asn Pro Lys Ala
        115             120             125

Ile Ile Tyr Phe Gly Ser Val Phe Ser Leu Phe Val Gly Asp Asn Val
    130             135             140

Gly Thr Thr Glu Arg Trp Gly Ile Phe Ala Leu Ile Ile Val Glu Thr
145             150             155             160

Leu Ala Trp Phe Thr Val Val Ala Ser Leu Phe Ala Leu Pro Gln Met
            165             170             175

Arg Arg Gly Tyr Gln Arg Leu Ala Lys Trp Ile Asp Gly Cys Ala Gly
        180             185             190

Ala Leu Phe Ala Gly Phe Gly Ile His Leu Ile Ile Ser Arg
        195             200             205
```

<210> SEQ ID NO 116
<211> LENGTH: 206
<212> TYPE: PRT
<213> ORGANISM: Artificial Sequence
<220> FEATURE:
<223> OTHER INFORMATION: Synthetic: efe rhtC L62S

<400> SEQUENCE: 116

```
Met Leu Met Leu Phe Leu Thr Val Ala Met Val His Ile Val Ala Leu
1               5               10              15

Met Ser Pro Gly Pro Asp Phe Phe Phe Val Ser Gln Thr Ala Val Ser
            20              25              30

Arg Ser Arg Lys Glu Ala Met Met Gly Val Leu Gly Ile Thr Cys Gly
        35              40              45

Val Met Val Trp Ala Gly Ile Ala Leu Leu Gly Leu His Ser Ile Ile
    50              55              60

Glu Lys Met Ala Trp Leu His Thr Leu Ile Met Val Gly Gly Gly Leu
65              70              75              80

Tyr Leu Cys Trp Met Gly Tyr Gln Met Leu Arg Gly Ala Leu Lys Lys
                85              90              95

Glu Ala Val Ser Ala Pro Ala Pro Gln Val Glu Leu Ala Lys Ser Gly
            100             105             110

Arg Ser Phe Leu Lys Gly Leu Leu Thr Asn Leu Ala Asn Pro Lys Ala
        115             120             125

Ile Ile Tyr Phe Gly Ser Val Phe Ser Leu Phe Val Gly Asp Asn Val
    130             135             140

Gly Thr Thr Glu Arg Trp Gly Ile Phe Ala Leu Ile Ile Val Glu Thr
145             150             155             160

Leu Ala Trp Phe Thr Val Val Ala Ser Leu Phe Ala Leu Pro Gln Met
            165             170             175

Arg Arg Gly Tyr Gln Arg Leu Ala Lys Trp Ile Asp Gly Cys Ala Gly
        180             185             190

Ala Leu Phe Ala Gly Phe Gly Ile His Leu Ile Ile Ser Arg
        195             200             205
```

L-THREONINE EXPORT PROTEIN VARIANT AND METHOD FOR PRODUCTION OF L-THREONINE USING SAME

CROSS-REFERENCE TO RELATED APPLICATIONS

The present application is a 35 U.S.C. § 371 national-phase filing of International Application No. PCT/KR2020/012154, filed on Sep. 9, 2020, which claims the benefit of Korean Patent Application No. 10-2019-0111509, filed on Sep. 9, 2019, both of which applications are incorporated herein by reference in their entirety.

INCORPORATION BY REFERENCE

This application contains a sequence listing entitled "059520 00026_ST25.txt." being submitted herein in ASCII format via EFS-Web, which is a copy of the sequence listing as filed in PCT/KR2020/012154, was modified on Nov. 29, 2021 and is 65,836 bytes in size.

TECHNICAL FIELD

The present disclosure relates to an L-threonine exporter variant and a method for producing L-threonine by using the same.

BACKGROUND ART

L-Threonine (L-Thr), which is an essential amino acid, has been widely used as a feed additive or the like, and has also been widely used as a raw material for pharmaceutical products, such as infusion solutions, and as a material for health food.

Currently, direct fermentation using microorganisms is mainly used for the production of L-threonine. As for the microorganisms used for the production of L-threonine, originally, selected strains exhibiting analog resistance through chemical or physical mutation were mainly used, but recombinant strains using genetic engineering techniques have been mainly used due to the rapid development of genetic recombination technology and the establishment of molecular-level regulatory mechanisms in the 1990s.

Meanwhile, the expression of a gene capable of exporting a particular amino acid has contributed to an increase in productivity of the corresponding amino acid in microorganisms. The enhancement of the L-lysine export gene (lysE) in a microorganism of *Corynebacterium* sp. has improved the productivity of lysine (WO 9723597 A2). A patent (EP 1016710 B1) discloses that the productivity of L-glutamic acid, L-lysine, L-threonine, L-alanine, L-histidine, L-proline, L-arginine, L-valine, and L-isoleucine was improved by enhancing yahN, yeaS, yfiK, and yggA genes, of which functions are not yet identified in *E. coli*.

DISCLOSURE

Technical Problem

The present inventors selected mutant rhtC for the improvement in L-threonine exporting ability of the L-threonine exporter (RhtC) encoded by rhtC, and verified that the amount of L-threonine production was significantly improved through the mutant, thereby completing the present disclosure.

Technical Solution

An object of the present disclosure is to provide an L-threonine exporter variant including a substitution with another amino acid at a position corresponding to the 53rd or 62nd position in the amino acid sequence of SEQ ID NO: 1, having no less than 80% and less than 100% sequence homology with the amino acid sequence of SEQ ID NO: 1, and having L-threonine exporting activity.

Another object of the present disclosure is to provide a polynucleotide encoding the L-threonine exporter variant.

Still another object of the present disclosure is to provide a vector including the polynucleotide.

Still another aspect of the present disclosure is to provide a microorganism producing L-threonine, the microorganism including any one or more of the L-threonine exporter variant, the polynucleotide encoding the variant, and the vector including the polynucleotide.

Still another aspect of the present disclosure is to provide a method for producing L-threonine, the method including culturing the microorganism in a medium.

Advantageous Effects

The culture of microorganisms producing L-threonine by using L-threonine exporter variants can produce high-yield L-threonine compared with microorganisms having an existing unmodified protein.

DETAILED DESCRIPTION OF THE INVENTION

The present disclosure will be specifically described as follows. Each description and embodiment disclosed in this disclosure may also be applied to other descriptions and embodiments. That is, all combinations of various elements disclosed in this disclosure fall within the scope of the present disclosure. Furthermore, the scope of the present disclosure is not limited by the specific description below.

In accordance with one aspect of the present disclosure for accomplishing the object, there is provided an L-threonine exporter variant including at least one amino acid substitution in the amino acid sequence of SEQ ID NO: 1.

Specifically, the present disclosure provides a protein variant in which i) the 53rd amino acid is substituted with another amino acid and/or ii) the 62nd amino acid is substituted with another amino acid in the amino acid sequence of SEQ ID NO: 1. The amino acid substitution may include i) a substitution of the 53rd amino acid with threonine, or ii) a substitution of the 62nd amino acid with an amino acid selected from serine, arginine, alanine, aspartic acid, lysine, proline, cysteine, glycine, threonine, isoleucine, tyrosine, valine, histidine, phenylalanine, methionine, glutamine, asparagine, glutamic acid, or tryptophan.

As used herein, the term "threonine (Thr)" refers to one of the essential amino acids that are not synthesized in the body and can only be supplied through food, wherein threonine constitutes mucin as an intestinal epithelium-protecting substance, and the deficiency of threonine may impair growth and cause weight loss. Threonine is widely used as a feed additive, a raw material for pharmaceutical products such as infusion solutions, a material for health food, and the like. Like other amino acids, threonine also has D-form and L-form stereoisomers, and most naturally occurring threonine forms exist as L-threonine (L-Thr), which is the L-form stereoisomer. Herein, threonine (Thr) can be used interchangeably with L-threonine (L-Thr).

As used herein, the term "L-threonine exporter" or "L-threonine efflux protein" refers to a protein that mediates the export of L-threonine out of cells, wherein the protein is known as an inner membrane protein having five transmembrane domains. The experimental topology analysis suggests that the C-terminus of L-threonine is present in the cytoplasm (Daley D O et al., Global topology analysis of the *Escherichia coli* inner membrane proteome, Science. 2005 May 27; 308(5726):1321-3.). The L-threonine exporter may be, for example, a protein including the amino acid sequence of SEQ ID NO: 1, SEQ ID NO: 113, or SEQ ID NO: 115. The protein including the amino acid sequence of SEQ ID NO: 1, SEQ ID NO: 113, or SEQ ID NO: 115 may be used interchangeably with a protein having the amino acid sequence of SEQ ID NO: 1, SEQ ID NO: 113, or SEQ ID NO: 115 or a protein consisting of the amino acid sequence of SEQ ID NO: 1, SEQ ID NO: 113, or SEQ ID NO: 115. Herein, the L-threonine exporter may be used interchangeably with RhtC protein or RhtC.

Herein, SEQ ID NO: 1, SEQ ID NO: 113, or SEQ ID NO: 115 refers to an amino acid sequence having L-threonine exporting ability. Specifically, SEQ ID NO: 1, SEQ ID NO: 113, or SEQ ID NO: 115 is a sequence of the protein with L-threonine exporting ability encoded by the rhtC gene. The amino acid sequence of SEQ ID NO: 1, SEQ ID NO: 113, or SEQ ID NO: 115 is available via NCBI Gen Bank, a known database. For example, SEQ ID NO: 1 may be derived from *Escherichia coli* (*E. coli*), SEQ ID NO: 13 may be derived from *Shigella flexneri*, and SEQ ID NO: 115 may be derived from *Escherichia fergusonii*, but these sequences are not limited thereto, and any amino acid sequence for a protein having the same activity as the proteins including these amino acid sequences may be included without limitation. SEQ ID NO: 113 or SEQ ID NO: 115 may have 99% homology with SEQ ID NO: 1, but is not limited thereto.

Although the protein having L-threonine exporting ability in the present disclosure is defined as a protein including the amino acid sequence of SEQ ID NO: 1, SEQ ID NO: 113, or SEQ ID NO: 115, it would be obvious to a person skilled in the art that such a protein does not exclude a mutation that may occur due to a meaningless sequence addition upstream or downstream of the amino acid sequence of SEQ ID NO: 1, SEQ ID NO: 113, or SEQ ID NO: 115, or a naturally occurring mutation, or a silent mutation therein and that such a protein corresponds to a protein having the L-threonine exporting ability of the present disclosure as long as the protein has activity equivalent or corresponding to that of the protein including the amino acid sequence of SEQ ID NO: 1, SEQ ID NO: 113, or SEQ ID NO: 115. Specifically, the protein having L-threonine exporting activity of the present disclosure may be a protein consisting of the amino acid sequence of SEQ ID NO: 1, SEQ ID NO: 113, or SEQ ID NO: 115, or the amino acid sequence having at least 80%, at least 85%, at least 90%, at least 95%, at least 96%, at least 97%, at least 98%, or at least 99% homology or identity therewith. In addition, it is obvious that any protein having an amino acid sequence with a deletion, a modification, a substitution, or an addition in a part thereof may also fall within the scope of the proteins of the present disclosure to be mutated, as long as the protein has an amino acid sequence with such a homology or identity and shows an effect corresponding to the above protein.

That is, although described as "protein or polypeptide having the amino acid sequence set forth in a particular sequence number" or "protein or polypeptide including the amino acid sequence set forth in a particular sequence number" in the present disclosure, a protein having an amino acid sequence having deletion, modification, substitution, or addition in a part thereof may also be used in the present disclosure, as long as the protein has an activity identical or corresponding to that of the polypeptide consisting of the amino acid sequence of the corresponding sequence number. For example, it is obvious that for a "polypeptide consisting of the amino acid sequence of SEQ ID NO: 1", any polypeptide may also fall within the "polypeptide consisting of the amino acid sequence of SEQ ID NO: 1" as long as the polypeptide has a sequence corresponding to SEQ ID NO: 1 or a sequence having activity identical or corresponding thereto.

As used herein, the term "variant" refers to a protein in which at least one amino acid in the conservative substitution and/or modification is different from that of the recited sequence but of which the functions or properties are maintained. A variant differs from an identified sequence by several amino acid substitutions, deletions, or additions. Such a variant can be usually identified by modifying one or more amino acids in the amino acid sequence of the protein and evaluating the properties of the modified protein. That is, the ability of a variant may be increased, unchanged, or reduced compared with that of its native protein. In addition, some variants may include those in which at least one part (e.g., an N-terminal leader sequence or a transmembrane domain) is removed. Other variants may include variants in which a part of the N-terminus and/or C-terminus of a mature protein is removed. The term "variant" may also be used interchangeably with "modification", "modified protein", "modified polypeptide", "mutant", "mutein", "divergent", or the like, and any term that is used in a sense of being mutated can be used without limitation thereto. For the purpose of the present disclosure, the variant may refer to those in which the activity of a mutated protein is increased compared with that of a natural wild-type or unmodified protein, but the variant is not limited thereto.

As used herein, the term "conservative substitution" refers to substitution of one amino acid with another amino acid that has similar structural and/or chemical properties. The variant may have, for example, one or more conservative substitutions while still retaining one or more biological activities. Such an amino acid substitution may generally occur based on similarities in polarity, charge, solubility, hydrophobicity, hydrophilicity, and/or amphipathic nature of residues. For example, among the electrically charged amino acids, positively charged (basic) amino acids include arginine, lysine, and histidine; and negatively charged (acidic) amino acids include glutamic acid and aspartic acid; and among the uncharged amino acids, nonpolar amino acids include glycine, alanine, valine, leucine, isoleucine, methionine, phenylalanine, tryptophan, and proline; polar or hydrophilic amino acids include serine, threonine, cysteine, tyrosine, asparagine, and glutamine; and among the polar amino acids, aromatic amino acids include phenylalanine, tryptophan, and tyrosine.

In addition, a variant may include deletions or additions of amino acids that have a minimal effect on the characteristics and secondary structure of a polypeptide. For example, a polypeptide may be conjugated to a signal (or leader) sequence of a protein N-terminus that is involved in the transfer of proteins co-translationally or post-translationally. In addition, the polypeptide may also be conjugated to another sequence or linker so as to be identified, purified, or synthesized.

The "substitution with another amino acid" is not limited as long as the amino acid differs from the amino acid before substitution. That is, when alanine, the 53rd amino acid, is substituted with an amino acid other than alanine, or leucine, the 62nd amino acid, is substituted with an amino acid other than leucine in the amino acid sequence of SEQ ID NO: 1, SEQ ID NO: 113, or SEQ ID NO: 115, such a substitution is not limited. As for the expression "a particular amino acid is substituted" in the present disclosure, it is obvious that the amino acid is substituted with an amino acid different from the amino acid before substitution, even if it is not specifically stated that the amino acid has been substituted with another amino acid.

The variant may be a variant in which at least one amino acid of the 53rd or 62nd amino acid is substituted with an amino acid different from the amino acid before substitution. Alternatively, the variant may be a variant having an uncharged amino acid, in which the substituted amino acid is different from the amino acid before substitution, but is not limited thereto.

Specifically, the variant may be a variant in which i) the 53rd amino acid is substituted with another amino acid or ii) the 62nd amino acid is substituted with another amino acid in the amino acid sequence of SEQ ID NO: 1, SEQ ID NO: 113, or SEQ ID NO: 115. The substitution with another amino acid may include i) a substitution of the 53rd amino acid with threonine, or ii) a substitution of the 62nd amino acid with an amino acid selected from serine, arginine, alanine, aspartic acid, lysine, proline, cysteine, glycine, threonine, isoleucine, tyrosine, valine, histidine, phenylalanine, methionine, glutamine, asparagine, glutamic acid, or tryptophan. More specifically, the variant may be a variant in which i) the 53rd amino acid is substituted with threonine, or ii) the 62nd amino acid is substituted with an amino acid selected from serine, arginine, alanine, aspartic acid, lysine, proline, cysteine, glycine, threonine, isoleucine, tyrosine, valine, histidine, phenylalanine, methionine, glutamine, asparagine, glutamic acid, or tryptophan in the amino acid sequence of SEQ ID NO: 1, SEQ ID NO: 113, or SEQ ID NO: 115.

The L-threonine exporter variant provided in the present disclosure may refer to a variant of which the L-threonine exporting ability is increased compared with that of the protein before mutation by a substitution of an amino acid at a specific position, among the aforementioned proteins having L-threonine exporting ability.

The variant having i) a substitution of the 53rd amino acid with threonine and ii) a substitution of the 62nd amino acid with another amino acid in the amino acid sequence of SEQ ID NO: 1, SEQ ID NO: 113, or SEQ ID NO: 115 may be a variant including any one amino acid sequence of SEQ ID NOS: 93 to 112, 114, and 116, specifically consisting essentially of any one amino acid sequence of SEQ ID NOS: 93 to 112, 114, and 116, and more specifically consisting of any one amino acid sequence of SEQ ID NOS: 93 to 112, 114, and 116.

The variant may be a variant which includes a substitution with another amino acid at a position corresponding to the 53rd or 62nd position in the amino acid sequence of SEQ ID NO: 1, SEQ ID NO: 113, or SEQ ID NO: 115, has at least 80%, 90%, 95%, 96%, 97%, 98%, or 99%, or less than 100% sequence homology with the amino acid sequence of SEQ ID NO: 1, SEQ ID NO: 113, or SEQ ID NO: 115, and has L-threonine exporting activity.

In addition, the variant may include any one amino acid sequence of SEQ ID NOS: 93 to 112, 114, and 116, or an amino acid sequence in which at least one amino acid selected from the 53rd or 62nd amino acid in the amino acid sequence is fixed and which has at least 80% homology or identity with the amino acid sequence, but is not limited thereto. Specifically, the variant of the present disclosure may include a polypeptide which has at least 80%, 90%, 95%, 96%, 97%, 98%, or 99% homology or identity with any one amino acid sequence of SEQ ID NOS: 93 to 112, 114, and 116. It is also obvious that any protein which has an amino acid sequence with a deletion, a modification, a substitution, or an addition in a part of the sequence other than the 53rd or 62nd amino acid positions can also fall within the scope of the present disclosure, as long as the amino acid sequence has such a homology or identity and exhibits an effect corresponding to the protein.

As used herein, the term "homology" or "identity" refers to a degree of relatedness between two given amino acid sequences or nucleotide sequences, and it may be expressed as a percentage. The terms homology and identity may often be used interchangeably.

The sequence homology or identity of conserved polynucleotides or polypeptides may be determined using a standard alignment algorithm, and default gap penalties established by a program to be used may be used together. Substantially, homologous or identical sequences may generally hybridize with each other along at least about 50%, 60%, 70%, 80%, or 90% of the entirety or the full length of the sequences under moderate or highly stringent conditions. In hybridization, polynucleotides containing a degenerate codon instead of a codon are also considered.

Whether any two polynucleotide or polypeptide sequences have homology, similarity, or identity may be determined using a known computer algorithm such as the "FASTA" program using default parameters, for example, Pearson et al. (1988) *Proc. Natl. Acad. Sci. USA* 85:2444. Alternatively, this may be determined using the Needleman-Wunsch algorithm (Needleman and Wunsch, 1970, *J. Mol. Biol.* 48:443-453), which is performed in the Needleman program of the European Molecular Biology Open Software Suite (EMBOSS) package (Rice et al., 2000, *Trends Genet.* 16:276-277) (version 5.0.0 or later) (GCG program package (including GCG program package (Devereux, J. et al., *Nucleic Acids Research* 12:387 (1984)), BLASTP, BLASTN, FASTA (Atschul, S. F. et al., *J MOLEC BIOL* 215:403 (1990); Guide to Huge Computers, Martin J. Bishop, ed., Academic Press, San Diego, 1994, and CARILLO et al. (1988) *SIAM J Applied Math* 48:1073). For example, the homology, similarity, or identity may be determined using BLAST from the National Center for Biotechnology Information database or ClustalW.

The homology, similarity, or identity of polynucleotides or polypeptides may be determined by comparing sequence information through the GAP computer program, for example, Needleman et al., (1970), *J Mol Biol.* 48:443, as disclosed in Smith and Waterman, *Adv. Appl. Math* (1981) 2:482. Briefly, the GAP program defines the homology, similarity, or identity as the value obtained by dividing the number of similarly aligned symbols (i.e., nucleotides or amino acids) by the total number of the symbols in the shorter of the two sequences. The default parameters for the GAP program may include: (1) a binary comparison matrix (containing a value 1 for identity and a value 0 for non-identity) and the weighted comparison matrix of Gribskov et al. (1986) *Nucl. Acids Res.* 14:6745 as disclosed in Schwartz and Dayhoff, eds., *Atlas Of Protein Sequence And Structure*, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps.

In addition, whether any two polynucleotide or polypeptide sequences have homology, similarity, or identity may be confirmed by comparing these sequences through Southern hybridization experiments to be performed under defined strict conditions, and the appropriate hybridization conditions to be defined may be determined within the scope of the art and by a method well known to those skilled in the art (e.g., J. Sambrook et al., *Molecular Cloning, A Laboratory Manual,* 2nd Edition, Cold Spring Harbor Laboratory Press, Cold Spring Harbor, N.Y., 1989; F. M. Ausubel et al., *Current Protocols in Molecular Biology*, John Wiley & Sons, Inc., New York).

As used herein, the term "L-threonine exporter variant" may be used interchangeably with a modified polypeptide having L-threonine producing ability, an L-threonine producing modified polypeptide, a modified polypeptide producing L-threonine, a modified polypeptide having L-threonine exporting activity, L-threonine export active variant, L-threonine exporting variant, mutant RhtC, and an RhtC variant, a mutant L-threonine exporter, or the like. The protein may be derived from *Escherichia coli* (*E. coli*), but is not limited thereto.

The L-threonine exporter variant may include a mutation at the 53rd and/or 62nd position in the amino acid sequence of SEQ ID NO: 1, SEQ ID NO: 113, or SEQ ID NO: 115, or any variant having an amino acid sequence with an addition or deletion of amino acid in the amino acid sequence of SEQ ID NO: 1, SEQ ID NO: 113, or SEQ ID NO: 115 may also fall within the scope of the present disclosure, as long as the variant includes a substitution of an amino acid at a position corresponding to the 53rd and/or 62nd amino acid from the N-terminus of SEQ ID NO: 1, SEQ ID NO: 113, or SEQ ID NO: 115. The L-threonine exporter variant may be a variant in which the 53rd and/or 62nd amino acid is substituted with another amino acid in the amino acid sequence of SEQ ID NO: 1, SEQ ID NO: 113, or SEQ ID NO: 115, or may be a mutant L-threonine exporter, which includes the amino acid sequence of SEQ ID NO: 1, SEQ ID NO: 113, or SEQ ID NO: 115 or has enhanced activity compared with a wild-type microorganism-derived L-threonine exporter before mutation. Such an L-threonine exporter variant refers to a variant in which, in the amino acid sequence of SEQ ID NO: 1, SEQ ID NO: 113, or SEQ ID NO: 115 or an amino acid sequence having at least 80%, 85%, 90%, 95%, 96%, 97%, 98%, or 99% homology or identity with the amino acid sequence of SEQ ID NO: 1, SEQ ID NO: 113, or SEQ ID NO: 115, an amino acid at a position corresponding to the 53rd or 62nd position of SEQ ID NO: 1, SEQ ID NO: 113, or SEQ ID NO: 115 is mutated.

The mutation of the 53rd or 62nd amino acid may be i) a substitution of the 53rd amino acid with threonine, or ii) a substitution of the 62nd amino acid with an amino acid selected from serine, arginine, alanine, aspartic acid, lysine, proline, cysteine, glycine, threonine, isoleucine, tyrosine, valine, histidine, phenylalanine, methionine, glutamine, asparagine, glutamic acid, or tryptophan.

Specifically, the L-threonine exporter variant may be a variant in which in the amino acid sequence of SEQ ID NO: 1, SEQ ID NO: 113, or SEQ ID NO: 115, i) the 53rd amino acid is substituted with threonine, or ii) the 62nd amino acid is substituted with an amino acid selected from serine, arginine, alanine, aspartic acid, lysine, proline, cysteine, glycine, threonine, isoleucine, tyrosine, valine, histidine, phenylalanine, methionine, glutamine, asparagine, glutamic acid, or tryptophan, and may be a variant which has enhanced activity compared with a protein including the amino acid sequence of SEQ ID NO: 1, SEQ ID NO: 113, or SEQ ID NO: 115 or a wild-type microorganism-derived L-threonine exporter before mutation.

For the purpose of the present disclosure, a microorganism including the L-threonine exporter variant shows an increase in amount of L-threonine production. This is significant in that the amount of L-threonine production can be increased by the L-threonine exporter variant of the present disclosure, whereas a wild-type microorganism cannot produce L-threonine, or, even if it can, it can only produce a very small amount of L-threonine.

In accordance with another aspect of the present disclosure, there is provided a polynucleotide encoding the L-threonine exporter variant.

The L-threonine, the protein including the amino acid sequence of SEQ ID NO: 1 and having L-threonine exporting activity, and the variant thereof are as described above.

As used herein, the term "polynucleotide" refers to a polymer of nucleotide units linked in a chain type through covalent linkage, and to a DNA or RNA strand having a predetermined length or longer. More specifically, the term refers to a polynucleotide fragment encoding the variant.

The polynucleotide encoding the L-threonine exporter variant of the present disclosure may include, without limitation, any polynucleotide sequence that encodes the modified polypeptide having L-threonine exporting activity of the present disclosure. In the present disclosure, the gene encoding the amino acid sequence of the L-threonine exporter is the rhtC gene, which may be derived from *Escherichia coli* (*E. coli*), *Shigella flexneri*, or *Escherichia fergusonii*, but is not limited thereto. In addition, the gene may be a nucleotide sequence encoding the amino acid sequence of SEQ ID NO: 1, SEQ ID NO: 113, or SEQ ID NO: 115, and more specifically, the nucleotide sequence encoding the amino acid sequence of SEQ ID NO: 1 may be a sequence including the nucleotide sequence of SEQ ID NO: 2, but is not limited thereto.

Specifically, the polynucleotide of the present disclosure may be variously modified in a coding region thereof within the range in which the amino acid sequence of the polypeptide is not altered, considering codon degeneracy or the codons preferred by an organism in which the polypeptide is to be expressed. Specifically, any polynucleotide sequence may be included without limitation as long as the polynucleotide sequence encodes the L-threonine exporter variant, in which the 53rd or 62nd amino acid is substituted with another amino acid sequence in the amino acid sequence of SEQ ID NO: 1, SEQ ID NO: 113, or SEQ ID NO: 115.

In addition, any sequence may be included without limitation as long as the sequence encodes a protein with L-threonine exporting activity, in which the 53rd or 62nd amino acid is substituted with another amino acid in the amino acid sequence of SEQ ID NO: 1, SEQ ID NO: 113, or SEQ ID NO: 115, by hybridizing with a probe that may be prepared from a known gene sequence, for example, a complementary sequence to the entirety or a part of the nucleotide sequence, under stringent conditions. The "stringent conditions" refer to conditions that enable specific hybridization between polynucleotides. Such conditions are specifically described in literature (see Sambrook et al., supra, 9.50-9.51, 11.7-11.8). For example, the conditions may include conditions under which genes having high homology or identity, such as genes having at least 40%, specifically at least 90%, more specifically at least 95%, still more specifically at least 97%, and still more specifically at least 99% homology or identity hybridize with each other, but genes having lower homology or identity do not hybridize with each other; or typical washing conditions for Southern hybridization, i.e., washing is conducted once, specifically twice or three times at a salt concentration and temperature corresponding to 60° C., 1×SSC, and 0.1% SDS, specifically 60° C., 0.1×SSC, and 0.1% SDS, and more specifically 68° C., 0.1×SSC, and 0.1% SDS.

Hybridization requires that two nucleic acids have complementary sequences, although mismatches between bases may be possible depending on hybridization stringency. The term "complementary" is used to describe the relationship between nucleotide bases that can hybridize with each another. For example, with respect to DNA, adenosine is complementary to thymine, and cytosine is complementary to guanine. Therefore, the present disclosure may include not only substantially similar nucleic acid sequences, but also isolated nucleic acid fragments complementary to the entire sequence.

Specifically, polynucleotides having homology or identity can be detected at a $T_m$ value of 55° C. using hybridization conditions that include a hybridization step and using the conditions described above. In addition, the $T_m$ value may be 60° C., 63° C., or 65° C., but is not limited thereto, and may be appropriately adjusted by a person skilled in the art according to the purpose.

The appropriate stringency for hybridizing polynucleotides depends on the length of the polynucleotides and the degree of complementarity thereof, and variables thereof are well known in the art (e.g., Sambrook et al., supra).

In accordance with another aspect of the present disclosure, there is provided a vector including the polynucleotide encoding the L-threonine exporter variant.

The L-threonine, the protein including the amino acid sequence of SEQ ID NO: 1 and having L-threonine exporting activity, and the variant thereof are as described above.

As used herein, the term "vector" refers to a DNA construct containing a nucleotide sequence of a polynucleotide encoding a target protein, which is operably linked to a suitable control sequence so that the target protein can be expressed in an appropriate host. The control sequence may include a promoter capable of initiating transcription, any operator sequence for controlling transcription, a sequence for encoding an appropriate mRNA ribosomal binding site, and sequences for controlling the termination of transcription and translation. The vector, after transformation into an appropriate host, may replicate or function irrespective of the genome of the host, or may be integrated into the genome itself.

The vector used in the present disclosure is not particularly limited, and any vector known in the art may be used. Examples of the vector commonly used may include native or recombinant plasmids, cosmids, viruses, and bacteriophages. For example, pWE15, M13, MBL3, MBL4, IXII, ASHII, APII, t10, t11, Charon4A, Charon21A, and the like may be used as phage vectors or cosmid vectors, and pBR-based, pUC-based, pBluescriptII-based, pGEM-based, pTZ-based, pCL-based, and pET-based vectors may be used as plasmid vectors. Specifically, pDZ, pACYC177, pACYC184, pCL, pECCG117, pUC19, pBR322, pMW118, pCC1BAC, or the like may be used.

For example, a polynucleotide encoding a target polypeptide may be inserted in a chromosome through a vector for intracellular chromosomal insertion. The insertion of the polynucleotide into the chromosome may be performed using any method known in the art, for example, homologous recombination, but is not limited thereto. The vector may further include a selection marker for identifying the insertion of the chromosome. A selection marker is used for selection of cells transformed with the vector, that is, to confirm whether the target nucleic acid molecule has been successfully inserted, and markers conferring selectable phenotypes, such as drug resistance, auxotrophy, resistance to cytotoxic drugs, and expression of surface proteins, may be used. Under the circumstances where selective agents are treated, only the cells capable of expressing the selection markers can survive or express other phenotypic traits, so that the transformed cells can be selected.

In accordance with still another aspect of the present disclosure, there is provided a microorganism producing L-threonine by including the L-threonine export variant or the polynucleotide encoding the variant.

As used herein, the term "microorganism including a modified polypeptide" or "microorganism including an L-threonine exporter variant" refers to a microorganism obtained by imparting L-threonine producing ability to a microorganism having naturally attenuated L-threonine producing ability or a parent strain without L-threonine producing ability. Specifically, the microorganism may be a microorganism expressing an L-threonine exporter variant including at least one amino acid mutation in the amino acid sequence of SEQ ID NO: 1, SEQ ID NO: 113, or SEQ ID NO: 115, wherein the amino acid mutation may include a substitution of the 53rd or 62nd amino acid from the N-terminus with another amino acid. Specifically, the microorganism may be a microorganism expressing a modified polypeptide in which the 53rd or 62nd amino acid is substituted with another amino acid in the amino acid sequence of SEQ ID NO: 1, SEQ ID NO: 113, or SEQ ID NO: 115 and which has L-threonine exporting activity, but is not limited thereto.

The L-threonine, the protein including the amino acid sequence of SEQ ID NO: 1 and having L-threonine exporting activity, and the variant thereof are as described above.

As used herein, the term "to be expressed/express" with respect to a protein refers to a state in which a target protein is introduced into a microorganism or a target protein is modified to be expressed in a microorganism. When the target protein is a protein present in a microorganism, the term refers to a state in which the activity of the protein is enhanced compared with the endogenous activity or the activity before modification of the protein. For the purpose of the present disclosure, the "target protein" may be the aforementioned protein variant having L-threonine exporting ability.

Specifically, the term "introduction of a protein" indicates that a microorganism exhibits the activity of a particular protein which was not originally possessed thereby or exhibits enhanced activity compared with the endogenous activity or the activity before modification of the corresponding protein. For example, the term may indicate that a polynucleotide encoding a particular protein is introduced into the chromosome of a microorganism or a vector including a polynucleotide encoding a particular protein is introduced into a microorganism, thereby exhibiting the activity of the particular protein. The term "enhancement of activity" indicates that the activity of a particular protein is enhanced compared with the endogenous activity or the activity before modification of the particular protein in the microorganism. The "endogenous activity" refers to the activity of a particular protein originally possessed by a parental strain before transformation thereof when a microorganism is transformed by genetic mutation caused by natural or artificial factors.

Specifically, the enhancement of activity in the present disclosure may be achieved by any one or more methods selected from the group consisting of: a method of increasing the intracellular copy number of a gene encoding the protein variant; a method of introducing a mutation into the expression control sequence of a gene encoding the protein variant; a method of replacing the expression control sequence of a gene encoding the protein variant having L-threonine exporting activity with a sequence having strong activity; a method of replacing a gene encoding a native protein having L-threonine exporting activity on the chromosome with a gene encoding the protein variant; a method of further introducing a mutation into a gene encoding the protein having an L-threonine exporting activity to enhance the activity of the protein variant; and a method of introducing a protein variant into a microorganism, but is not limited thereto.

In the above, the increasing of the copy number of a gene may be performed in a manner in which the gene is operably linked to a vector or by inserting the gene into the chromosome of a host cell, but is not particularly limited thereto. Specifically, a vector to which the polynucleotide encoding the protein of the present disclosure is operably linked and which can replicate and function irrespective of a host cell may be introduced into the host cell. Alternatively, a vector to which the polynucleotide is operably linked and which can insert the polynucleotide into the chromosome of the host cell may be introduced into the chromosome of the host cell. The insertion of the polynucleotide into the chromosome may be achieved by any method known in the art, for example, homologous recombination.

Next, the modifying of the expression control sequence to increase the expression of a polynucleotide may be performed by inducing the mutation of the sequence of a nucleic acid through a deletion, an insertion, a non-conservative or conservative substitution, or a combination thereof to further enhance the activity of the expression control sequence, or by replacing the expression control sequence with a nucleic acid sequence with a stronger activity, but is not particularly limited thereto. The expression control sequence may include a promoter, an operator sequence, a sequence for encoding a ribosome binding site, sequences for controlling the termination of transcription and translation, and the like, but is not particularly limited thereto.

A strong promoter, instead of the native promoter, may be linked to an upstream region of the expression unit of the polynucleotide, but is not limited thereto. Known examples of the strong promoter may include cj1 to cj7 promoters (Korean Patent No. 10-0620092), a lac promoter, a trp promoter, a trc promoter, a tac promoter, a lambda phage PR promoter, a PL promoter, a tet promoter, a gapA promoter, an SPL7 promoter, an SPL13 (sm3) promoter (Korean Patent No. 10-1783170), an 02 promoter (Korean Patent No. 10-1632642), a tkt promoter, a yccA promoter, and the like, but are not limited thereto.

Furthermore, the modifying of a polynucleotide sequence on the chromosome may be performed by inducing a mutation on the expression control sequence through a deletion, an insertion, a non-conservative or conservative substitution, or a combination thereof to further enhance the activity of the polynucleotide sequence, or by replacing the polynucleotide sequence with a polynucleotide sequence modified to have stronger activity, but is not particularly limited thereto.

Such introduction and enhancement of protein activity may generally increase the activity or concentration of the corresponding protein by at least 1%, at least 10%, at least 25%, at least 50%, at least 75%, at least 100%, at least 150%, at least 200%, at least 300%, at least 400%, or at least 500%, and up to 1,000% or 2,000% relative to the activity or concentration of the protein in a wild-type or non-modified microorganism strain, but is not limited thereto.

As used herein, the term "non-modified microorganism" refers to a native strain itself, a microorganism not containing the L-threonine exporter variant, or a microorganism not transformed with a vector including a polynucleotide encoding the L-threonine exporter variant, and does not exclude a strain containing mutation that may naturally occur in the microorganism.

In the present disclosure, the microorganism containing the L-threonine export variant or a polynucleotide encoding the variant may be a recombinant microorganism prepared by transformation with a vector including the polynucleotide, but is not limited thereto.

As used herein, the term "transformation" indicates that a vector containing a polynucleotide encoding a target protein is introduced into a host cell to express the protein encoded by the polynucleotide in the host cell. The transformed polynucleotide may be any polypeptide as long as the polypeptide can be expressed in a host cell, regardless of whether the polynucleotide is inserted and located on the chromosome of the host cell or located outside of the chromosome. In addition, the polynucleotide includes DNA and RNA encoding the target protein. The polynucleotide may be introduced in any shape as long as the polynucleotide can be introduced and expressed in the host cell. For example, the polynucleotide may be introduced in the form of an expression cassette, which is a gene construct containing all factors required for self-expression. The expression cassette may include a promoter, a transcription termination signal, a ribosome binding site, and a translation termination signal, which may be operably linked to the polynucleotide. The expression cassette may be an expression vector enabling self-replication. In addition, the polynucleotide may be introduced in the form as it is into the host cell to be operably linked to the sequences required for expression in the host cell, but is not limited thereto.

In addition, the term "operably linked" refers to a functional linkage between a gene sequence and a promoter sequence which initiates and mediates the transcription of the polynucleotide encoding the desired polypeptide of the present disclosure.

As used herein, the term "microorganism producing L-threonine" encompasses all of microorganisms with naturally or artificially occurring genetic modification, and refers to a microorganism in which a particular mechanism is attenuated or enhanced due to the insertion of an exogenous gene or the enhancement or inactivation of activity of an endogenous gene, wherein the microorganism has genetic mutation or enhanced activity for the production of desired L-threonine. For the purpose of the present disclosure, the microorganism producing L-threonine may indicate a microorganism, which can produce desired L-threonine in excess from a carbon source in a medium, compared with wild-type or non-modified microorganisms, by containing the L-threonine exporter variant. In the present disclosure, the "microorganism producing L-threonine" may be used interchangeably with "microorganism having L-threonine producing ability" or "L-threonine producing microorganism".

The microorganism producing L-threonine may be a recombinant microorganism. The recombinant microorganism is as described above.

The microorganism producing L-threonine is not particularly limited to the species thereof as long as the microorganism can produce L-threonine. Specifically, the microorganism producing L-threonine may include microorganisms belonging to *Corynebacterium* sp., *Escherichia* sp., *Enterobacter* sp., *Erwinia* sp., *Serratia* sp., *Providencia* sp., and *Brevibacterium* sp., and more specifically a microorganism belonging to *Corynebacterium* sp. or *Escherichia* sp.

More specifically, the microorganism of *Escherichia* sp. may be *Escherichia* coil; and the microorganism of *Corynebacterium* sp. may be *Corynebacterium glutamicum*, *Corynebacterium ammoniagenes*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium pollutisoli*, *Corynebacterium imitans*, *Corynebacterium testudinoris*, *Corynebacterium flavescens*, or the like, and specifically *Corynebacterium glutamicum*. However, any microorganism belonging to *Escherichia* sp. or *Corynebacterium* sp. may be included without limitation as long as the microorganism can increase the amount of L-threonine production through the introduction or enhancement of a protein having L-threonine exporting activity.

In the present disclosure, a parent strain of the microorganism producing L-threonine, which is modified to express the protein having L-threonine exporting activity or the protein variant is not particularly limited as long as the parent strain is a microorganism producing L-threonine. The microorganism producing L-threonine may be a microorganism in which, for increasing the amount of L-threonine production, the biosynthesis pathway of L-threonine is enhanced, the feedback inhibition for L-threonine is canceled, a gene attenuating the biosynthesis pathway of L-threonine is inactivated, the activity of the L-threonine operon is increased, and/or the resistance to an L-threonine analog is imparted.

Specifically, for the enhancing of the biosynthesis pathway of L-threonine, for example, the expression of the thrC gene encoding threonine synthase, the ppc gene encoding phosphoenolpyruvate carboxylase, the galP gene involved in glucose uptake, the lysC gene encoding lysine-sensitive aspartokinase 3, the hom gene encoding homoserine dehydrogenase, or the pyc gene inducing an increase in oxaloacetate pool may be enhanced or increased in the microorganism.

For the canceling of the feedback inhibition for L-threonine, for example, a genetic mutation for the lysC gene, the hom gene, the thrA gene having bifunctional aspartokinase/homoserine dehydrogenase 1, or the like may be introduced into the microorganism.

For the inactivating of a gene attenuating the bio-synthesis pathway of L-threonine, for example, the expression of the pckA gene involved in the conversion of oxaloacetate (OAA), an intermediate in the L-threonine biosynthesis, into phosphoenolpyruvate (PEP); the tyrR gene inhibiting the lysC gene; the galR gene inhibiting the expression of the galP gene involved in glucose uptake, or the mcbR gene, which is a DNA-binding transcriptional dual regulator, may be attenuated or inactivated in the microorganism.

For the increasing of the activity of the L-threonine operon, a plasmid including a threonine operon composed of genes encoding aspartokinase, homoserine dehydrogenase, homoserine kinase, and threonine synthase (Japanese Patent Publication No. 2005-227977), an *E. coli*-derived threonine operon, or the like may be introduced into the microorganism (TURBA E. et al., *Agric. Biol. Chem.* 53:2269-2271, 1989), thereby increasing the expression of the threonine operon in the microorganism.

In addition, the microorganism may have resistance to α-amino-β-hydroxy valeric acid or D,L-threonine hydroxamate, which are L-threonine analogs.

However, without limitation thereto, the L-threonine producing ability can be enhanced by way of a gene expression control method known in the art.

As used herein, the term "enhancement/increase" includes a concept encompassing all types of actions of increasing activity compared with the endogenous activity.

Such enhancement or increase in gene activity can be achieved by application of various methods well known in the art. The enhancement or increase may be achieved by any one or more methods selected from the group consisting of: a method of increasing the intracellular copy number of a gene; a method of introducing a mutation into the expression control sequence of a gene; a method of replacing the expression control sequence of a gene with a sequence having strong activity; a method of further introducing a mutation into a gene to enhance the activity of the corresponding gene; and a method of introducing an exogenous gene into the microorganism, and may be achieved by a combination thereof, but are not particularly limited thereto.

As used herein, the term "inactivation" includes a concept encompassing all of the attenuation of activity or the absence of activity compared with the endogenous activity.

Such inactivation of gene activity can be achieved by application of various methods well known in the art. Examples of the methods may include: a method of deleting the entirety or a part of a gene on a chromosome, including the elimination of the activity of the gene; a method of replacing a gene encoding a protein on a chromosome with a gene mutated to reduce the activity of the protein; a method of introducing a mutation into the expression control sequence of the gene on the chromosome encoding the protein; a method of replacing the expression control sequence of the gene encoding the protein with a sequence with attenuation or absence of activity (e.g., a method of replacing a promoter of the gene with a promoter weaker than the endogenous promoter); a method of deleting the entirety or a part of the gene on the chromosome encoding the protein; a method of introducing an antisense oligonucleotide (e.g., antisense RNA) that complementarily binds to the transcriptome of the gene on the chromosome and inhibits the translation from mRNA to a protein; a method of making the attachment of ribosomes impossible by artificially adding a sequence complementary to the SD sequence upstream of the SD sequence of the gene encoding the protein to form a secondary structure; and a reverse transcription engineering (RTE) method of adding a promoter to the 3' end of the open reading frame (ORF) of the corresponding sequence to be reverse transcribed. The inactivation of gene activity may be achieved by a combination of the methods, but is not particularly limited thereto.

In accordance with still another aspect of the present disclosure, there is provided a method for producing L-threonine, the method including a step of culturing in a medium the microorganism producing L-threonine.

The L-threonine, the protein including the amino acid sequence of SEQ ID NO: 1 and having L-threonine exporting activity, the variant thereof, the expression of the protein, and the microorganism are as described above.

As used herein, the term "culture" refers to growing the microorganism in appropriately adjusted environmental conditions. The culture procedure of the present disclosure may be performed according to appropriate media or culture conditions known in the art. Such a culture procedure may be easily adjusted according to the selected strain by a person skilled in the art. Specifically, examples of the culture may include a batch culture, a continuous culture, and a fed-batch culture, but are not limited thereto.

As used herein, the "medium" refers to a mixture containing as main ingredients nutrient substances required for the culture of the microorganism, wherein the medium supplies nutrient substances, growth factors, and the like, including water, which is essential for survival and growth. Specifically, as for the media and other culture conditions used for culturing the microorganism of the present disclosure, any medium that is used for typical culture of microorganisms may be used without particular limitation. However, the microorganisms of the present disclosure may be cultured under aerobic conditions in a conventional medium containing appropriate carbon sources, nitrogen sources, phosphorus sources, inorganic compounds, amino acids, and/or vitamins, while the temperature, pH, and the like are adjusted.

In the present disclosure, the carbon source may include carbohydrates, such as glucose, fructose, sucrose, and maltose; sugar alcohols, such as mannitol and sorbitol; organic acids, such as pyruvic acid, lactic acid, and citric acid; amino acids, such as glutamic acid, methionine, and lysine; and the like. In addition, natural organic nutrient sources, such as starch hydrolysates, molasses, blackstrap molasses, rice bran, cassava, bagasse, and corn steep liquor, may be used, and specifically, carbohydrates, such as glucose and sterile pretreated molasses (i.e., molasses converted to reduced sugars) may be used, and appropriate amounts of other carbon sources may be used without limitation. These carbon sources may be used alone or in a combination of two or more, but are not limited thereto.

As for the nitrogen sources, inorganic nitrogen sources, such as ammonia, ammonium sulfate, ammonium chloride, ammonium acetate, ammonium phosphate, ammonium carbonate, and ammonium nitrate; amino acids, such as glutamic acid, methionine, and glutamine; and organic nitrogen sources, such as peptone, NZ-amine, meat extracts, yeast extracts, malt extracts, corn steep liquor, casein hydrolysates, fishes or their decomposition products, defatted soybean cake or its decomposition products, and the like may be used. These nitrogen sources may be used alone or in a combination of two or more, but are not limited thereto.

The phosphate sources may include potassium phosphate monobasic, potassium phosphate dibasic, and corresponding sodium-containing salts. As for inorganic compounds, sodium chloride, calcium chloride, iron chloride, magnesium sulfate, iron sulfate, manganese sulfate, calcium carbonate, and the like may be used, and besides, amino acids, vitamins, and/or suitable precursors may be included. These sources or precursors may be added to the medium in a batch or continuous manner. However, the medium of the present disclosure is not limited thereto.

In the present disclosure, the pH of the medium may be adjusted by adding compounds, such as ammonium hydroxide, potassium hydroxide, ammonia, phosphoric acid, and sulfuric acid, to the medium in an appropriate manner during the culture of the microorganism. In addition, a defoaming agent, such as a fatty acid polyglycol ester, may be added to suppress foam formation. In addition, oxygen or oxygen-containing gas may be injected into the medium to maintain the aerobic state of the medium, or nitrogen, hydrogen, or carbon dioxide gas or no gas may be injected to maintain the anaerobic or non-aerobic state of the medium, but the medium is not limited thereto.

The temperature of the medium may be 20° C. to 50° C., and specifically 30° C. to 37° C., but is not limited thereto.

The culture period may continue until a desired amount of a useful substance produced can be obtained, and may be specifically 10 to 100 hours, but is not limited thereto.

L-Threonine produced by the culture may be released into the medium or may remain in cells without being released.

The method for producing L-threonine may include a step of recovering L-threonine from the cultured microorganism or medium.

The recovering of L-threonine produced in the culturing step may be collecting desired L-threonine from the culture by using an appropriate method known in the art according to the culturing method. For example, centrifugation, filtration, anion-exchange chromatography, crystallization, HPLC, and the like may be used, and desired L-threonine can be recovered from the medium or microorganism by using an appropriate method known in the art.

In addition, the recovering step may include a purification process, and may be performed using an appropriate method known in the art. Therefore, the recovered L-threonine may be in a purified form or in a form of a microorganism fermentation broth containing L-threonine (*Introduction to Biotechnology and Genetic Engineering*, A. J. Nair, 2008).

MODE FOR CARRYING OUT THE INVENTION

Hereinafter, the present disclosure will be described in detail with reference to exemplary embodiments. However, these exemplary embodiments are given for specifically illustrating the present disclosure, and the scope of the present disclosure is not limited thereto.

Example 1: Construction of L-Threonine Exporter Mutant Libraries and Plasmids To prepare a template to be used in error-prone PCR, nucleotide sequence fragments were obtained from the *Escherichia coli* W3110 genomic DNA by performing PCR using SEQ ID NO: 43 and SEQ ID NO: 44.

```
(rhtC F)
                                    SEQ ID NO: 43
GTCGACTCTAGAGGATCCCCGCTGATTCGTGCGCATGTTG (rhtC R)
                                    SEQ ID NO: 44
TGAATTCGAGCTCGGTACCCTCACCGCGAAATAATCAAAT
```

The pCL1920 digested with SmaI restriction enzyme (*Nucleic Acids Research,* 18, (1990) 4631) and the obtained DNA fragments were cloned using the Gibson assembly method to obtain pCL1920-Pn_rhtC as a recombinant plasmid. The cloning was performed by mixing the Gibson assembly reagent and each of the gene fragments in a calculated number of moles, followed by preservation at 50° C. for 1 hour.

Error-prone PCR was performed on wild-type rhtC encoding the L-threonine exporter for a random mutagenesis system, and in the error-prone PCR, the Diversify PCR random mutagenesis kit (Takara) was used. For the selection of mutation rate conditions, error-prone PCR was performed according to the $MnSO_4$ concentration in the two conditions as below. The aforementioned pCL1920-Pn_rhtC was used as a DNA template into which mutation was to be introduced. The constitution of the composition for error-prone PCR are as shown in Table 1. The conditions for PCR were as follows: denaturation at 95° C. for 30 minutes, 25 cycles of denaturation at 95° C. for 30 minutes, annealing at 55° C. for 30 seconds, and polymerization at 68° C. for 30 seconds, and polymerization at 68° C. for 60 seconds. SEQ ID NOS: 43 and 44 were used for primers.

TABLE 1

| case # | 1 (μL) | 2 (μL) |
|---|---|---|
| 10X Titanium taq Buffer | 5 | 5 |
| MnSO₄ (8 mM) | 1 | 2 |
| dGTP (2 mM) | 1 | 1 |
| 50 X dNTP Mix | 1 | 1 |
| Titanium Taq Polymerase | 1 | 1 |
| Forward primer (5 pmol) | 2 | 2 |
| Reverse primer (5 pmol) | 2 | 2 |
| Template DNA | 1 | 1 |
| dH₂O | 36 | 35 |
| Total | 50 | 50 |

A recombinant mutant plasmid library was obtained via the Gibson assembly method using DNA, from which the template plasmid was removed by subjecting the products of the error-prone PCR performed under the conditions of Table 1, to DpnI treatment, and pCL1920 digested with SmaI restriction enzyme. The mutant library, pCL1920-Pn_rhtC, and pCL1920, obtained via the above methods, were transformed into *Escherichia coli* K12 cells, and the cells were plated on LB plate media containing 50 μg/L spectinomycin. Fifty colonies were selected from K12 transformed with the mutation library, and sequencing was performed to determine the mutation rate and the occurrence or non-occurrence of mutations at various locations. As a result of sequencing, the mutation rate was 1.2 kb⁻¹ in the case #1 condition and 2.0 kb⁻¹ in the case #2 condition. Both cases #1 and #2 were determined to satisfy the mutation rate suitable for securing a mutant library, and thus effective mutation selection was performed using the library prepared under the above conditions. After 300 μL of M9 minimal media containing 60 g/L L-threonine was dispensed on 96-deep-well plates, the previously transformed K12/pCL1920-Pn_rhtC, K12/pCL1920, and K12/mutant library colonies were inoculated. The cells were cultured in the conditions of 1200 rpm/15 hr/37° C., followed by OD measurement at a wavelength of 600 nm. It was considered that a strain with significantly improved threonine exporting ability could grow at an L-threonine concentration of 60 g/L since the wild-type *E. coli* K12 strain generally undergoes growth inhibition in M9 media at around 30 g/L, which is the L-threonine minimal inhibition concentration (MIC). Most of the mutant strain libraries showed little growth in the deep-well plates like control strains (K12/pCL1920 and K12/pCL1920-Pn_rhtC), but four species of strains, of which growth was observed in contrast to those of the control strains, were selected, and OD for each was recorded.

TABLE 2

| Strain name | OD |
|---|---|
| K12/pCL1920 | 0.15 |
| K12/pCL1920-Pn_rhtC | 0.16 |
| K12/pCL1920-Pn_rhtC mutant library (3-1 C5) | 1.41 |
| K12/pCL1920-Pn_rhtC mutant library (3-2 D11) | 2.60 |
| K12/pCL1920-Pn_rhtC mutant library (3-4 E3) | 2.46 |
| K12/pCL1920-Pn_rhtC mutant library (3-4 G2) | 2.57 |

After pCL1920-Pn_rhtC mutant plasmids were extracted from the four species of selected mutant strains, sequencing was performed to check mutation, and the occurrence of mutation was confirmed in the coding sequence (CDS) but not the promoter region. The mutant plasmids mentioned in Table 2 were named pCL1920-Pn_rhtC(m1), pCL1920-Pn_rhtC(m2), pCL1920-Pn_rhtC(m3), and pCL1920-Pn_rhtC(m4) from the above.

In order to compare and evaluate the activity of mutant rhtC in the *Corynebacterium* strain, plasmids for inserting were prepared via the following method.

For homologous recombination, the upstream and downstream regions of Ncgl2533 were amplified using SEQ ID NOS: 45 and 46 and SEQ ID NOS: 51 and 52, respectively. In order to utilize the gapA promoter as a promoter of mutant rhtC, PCR was performed using the genomic DNA of *Corynebacterium glutamicum* ATCC13032 as a template together with the primers of SEQ ID NO: 47 and SEQ ID NO: 48. In order to secure fragments of the selected mutant rhtC in Table 2, rhtC, rhtC(m1), rhtC(m2), rhtC(m3), and rhtC(m4) fragments were separately obtained using the primers of SEQ ID NO: 47 and SEQ ID NO: 48.

```
(Ncgl2533 up F)
                                  SEQ ID NO: 45
TCGAGCTCGGTACCCCAGCAAGATCTAGTCATCAA (Ncgl2533 up R)
                                  SEQ ID NO: 46
GTCGTTTTTAGGCTTCCGCTGGAAAACATTTTGCA (PgapA F)
                                  SEQ ID NO: 47
AATGTTTTCCAGCGGAAGCCTAAAAACGACCGAGC (PgapA R)
                                  SEQ ID NO: 48
AAATAACATCAACATGTTGTGTCTCCTCTAAAGAT (rhtC_m F)
                                  SEQ ID NO: 49
TAGAGGAGACACAACATGTTGATGTTATTTCTCAC (rhtC_m R)
                                  SEQ ID NO: 50
TAAGCAGGTTGATTTTCACCGCGAAATAATCAAAT (Ncgl2533 dn F)
                                  SEQ ID NO: 51
ATTATTTCGCGGTGAAAATCAACCTGCTTAGGCGT (Ncgl2533 dn R)
                                  SEQ ID NO: 52
CTCTAGAGGATCCCCTATAGCTACCATCTGGGTGG
```

The PCR fragments obtained via the above procedure and the pDZ vector for chromosomal transformation digested with SmaI restriction enzyme were cloned using the Gibson assembly method to thereby obtain the wild-type plasmid and five mutant rhtC recombinant plasmids. The cloning was performed by mixing the Gibson assembly reagent and each of the gene fragments in a calculated number of moles, followed by preservation at 50° C. for 1 hour. The prepared plasmids were named pDZ-PgapA_rhtC, pDZ-PgapA_rhtC(m1), pDZ-PgapA_rhtC(m2), pDZ-PgapA_rhtC(m3), and pDZ-PgapA_rhtC(m4), respectively.

Example 2: Preparation of L-Threonine-Producing Strains 2-1: Mutant Lysine-Sensitive Aspartokinase 3 (LysC) Transformation The enhancement of the expression of the lysC gene corresponding to lysine-sensitive aspartokinase 3 and the mutation (L377K) trait for canceling the feedback inhibition on L-lysine and L-threonine (Korean Patent Publication No. 10-2019-0003019) were to be introduced. Specifically, the upstream region of the lysC promoter for homologous recombination on the chromosome and the downstream region of the 377th mutation of lysC were obtained, and via PCR using the genomic DNA of *Corynebacterium glutamicum* ATCC13032 as a template, the gene fragment of the upstream region of the lysC promoter was obtained through the primers of SEQ ID NO: 3 and SEQ ID NO: 4, and the gene fragment of the downstream region of the 377th mutation of lysC was obtained through the primers of SEQ ID NO: 9 and SEQ ID NO: 10.

```
(lysC promoter Up 1)
                                   SEQ ID NO: 3
TCGAGCTCGGTACCCGACAGGACAAGCACTGGTTG (lysC promoter Up 2)
                                   SEQ ID NO: 4
AGTAGCGCTGGGATGTTTCTCTTTGTGCACCTTTC (lysC Down 1)
                                   SEQ ID NO: 9
GAACATCGAAAAGATTTCCACCTCTGAGAT (lysC Down 2)
                                   SEQ ID NO: 10
CTCTAGAGGATCCCCGTTCACCTCAGAGACGATTA
```

In addition, the Pcj7 promoter fragment was obtained via PCR using the pECCG117-Pcj7-GFP plasmid (Korean Patent No. 10-0620092) as a template along with the primers of SEQ ID NO: 5 and SEQ ID NO: 6.

```
(Pcj7 1)
                                   SEQ ID NO: 5
GAAAGGTGCACAAAGAGAAACATCCCAGCGCTACT (Pcj7 2)
                                   SEQ ID NO: 6
TACGACCAGGGCCATGAGTGTTTCCTTTCGTTGGG
```

The gene fragment of the upstream region of the lysC L377K mutation was obtained via PCR using the genomic DNA of *Corynebacterium glutamicum* ATCC13032 as a template along with the primers of SEQ ID NO: 7 and SEQ ID NO: 8.

```
(lysC 1)
                                   SEQ ID NO: 7
CGAAAGGAAACACTCATGGCCCTGGTCGTACAGAA (lysC 2)
                                   SEQ ID NO: 8
GGTGGAAATCTTTTCGATGTTCACGTTGAC
```

PCR was performed by using Solg™ Pfu-X DNA polymerase as the polymerase and the following conditions: denaturation at 95° C. for 5 minutes; 30 cycles of denaturation at 95° C. for 30 seconds, annealing at 60° C. for 30 seconds, and polymerization at 72° C. for 60 seconds; and polymerization at 72° C. for 5 minutes.

The four PCR fragments obtained via the above procedure and the vector pDZ for chromosomal transformation digested with SmaI restriction enzyme (Korean Patent No. 10-1126041) were cloned using the Gibson assembly method (DG Gibson et al., *NATURE METHODS*, Vol. 6 No. 5, May 2009, NEBuilder HiFi DNA Assembly Master Mix) to thereby obtain a recombinant plasmid, which was named pDZ-Pcj7_lysC L377K. The cloning was performed by mixing the Gibson assembly reagent and each of the gene fragments in a calculated number of moles, followed by preservation at 50° C. for 1 hour.

The constructed pDZ-Pcj7_lysC L377K vector was transformed into a wild-type *Corynebacterium glutamicum* ATCC13032 strain by electroporation (*Appl. Microbiol. Biotechnol.* (1999) 52:541-545) and then subjected to secondary crossover to obtain a strain in which the wild-type lysC gene was replaced with the mutant Pcj7_lysC L377K gene on the chromosome. The corresponding genetic manipulation was confirmed through genome sequencing and PCR using the primers of SEQ ID NO: 11 and SEQ ID NO: 12 capable of respectively amplifying the outside sites of the upstream and downstream regions of homologous recombination where the corresponding gene was inserted.

```
(confirm lysC 1)
                                   SEQ ID NO: 11
ACATTCCACCCATTACTGCA (confirm lysC 2)
                                   SEQ ID NO: 12
TCTTCATCGGTTTCGAAGGT
```

The obtained transformed strain was named Cgl-TH-1.

2-2: Mutant Homoserine Dehydrogenase (Hom) Transformation

In order to cancel the regulation of mcbR, which is a DNA-binding transcriptional dual regulator, and to increase the expression level of hom corresponding to homoserine dehydrogenase, the hom promoter was replaced with the Pcj7 promoter. Furthermore, the L-threonine production was to be increased by applying, to Cgl-TH-1, the mutations (G378E, R398Q) for canceling the feedback inhibition of hom on L-threonine. For the transformation of the mutant hom, pDZ-Pcj7_hom(G378E, R398Q) was constructed. In order to replace the Pcj7 promoter for the hom promoter, the upstream region of the hom promoter for homologous recombination was obtained. Specifically, the fragment of the upstream region of the hom promoter was obtained via PCR using the genomic DNA of *Corynebacterium glutamicum* 13032 as a template along with the primers of SEQ ID NO: 14 and SEQ ID NO: 55.

```
(up F)
                                   SEQ ID NO: 14
TCGAGCTCGGTACCCTGTCTCCGTATGCAGTGAGC (up R)
                                   SEQ ID NO: 55
GGATGTTTCTTTGGAGCTTCGCTCAATCAT
```

The fragment of the Pcj7 promoter was obtained via PCR using the pECCG117-Pcj7-GFP plasmid (Korean Patent No. 10-0620092) as a template along with the primers of SEQ ID NO: 13 and SEQ ID NO: 56.

```
(cj7 F)
                                   SEQ ID NO: 13
GAAGCTCCAAAGAAACATCCCAGCGCTACT (cj7 R)
                                   SEQ ID NO: 56
AGATGCTGAGGTCATGATTGTTCTCCTATAATCGC
```

In order to apply the hom mutations (G378E, R398Q), the upstream region of the 1st to 378th amino acid hom coding sequence, the sequence including the G378E/R398Q mutations, and the downstream sequence of R398Q were obtained.

Specifically, the fragment of the 1st to 378th amino acid hom coding sequence was obtained via PCR using the genomic DNA of *Corynebacterium glutamicum* 13032 as a template along with the primers of SEQ ID NO: 17 and SEQ ID NO: 18. By way of the same method, PCR was performed using the genomic DNA of *Corynebacterium glutamicum* 13032 as a template along with the primers of SEQ ID NO: 15 and SEQ ID NO: 20, and the fragment of the sequence including the hom G378E/R398Q mutations. In addition, PCR was performed using the genomic DNA of *Corynebacterium glutamicum* 13032 as a template along with the primers of SEQ ID NO: 19 and SEQ ID NO: 21, and the fragment of the downstream sequence of hom R398Q for homologous recombination was obtained.

```
(hom F)
                                   SEQ ID NO: 17
TATAGGAGAACAATCATGACCTCAGCATCTGCCCC (G378E R)
                                   SEQ ID NO: 18
GCCAAAACCTCCACGCGATCTT (G378E F)
                                   SEQ ID NO: 15
AAGATCGCGTGGAGGTTTTGGC (R398Q R)
                                   SEQ ID NO: 20
GCGCTCTTCCTGTTGGATTGTACGC (R398Q F)
                                   SEQ ID NO: 19
GCGTACAATCCAACAGGAAGAGCGC (hom R)
                                   SEQ ID NO: 21
CTCTAGAGGATCCCCGACTGCGGAATGTTGTTGTG
```

The five PCR fragments obtained via the above procedure and the vector pDZ for chromosomal transformation digested with SmaI restriction enzyme were cloned using the Gibson assembly method to thereby obtain a recombinant plasmid, which was named pDZ-Pcj7_hom(G378E, R398Q). The cloning was performed by mixing the Gibson assembly reagent and each of the gene fragments in a calculated number of moles, followed by preservation at 50° C. for 1 hour.

The prepared pDZ-Pcj7_hom(G378E, R398Q) vector was transformed into the Cgl-TH-1 strain by electroporation and then subjected to secondary crossover to obtain a strain in which the wild-type hom gene was replaced with the mutant Pcj7_hom(G378E, R398Q) gene on the chromosome. The corresponding genetic manipulation was confirmed through genome sequencing and PCR using SEQ ID NO: 22 and SEQ ID NO: 23 capable of respectively amplifying the outside sites of the upstream and downstream regions of homologous recombination where the corresponding gene was inserted.

```
(hom conf F)
                                   SEQ ID NO: 22
TGGGTAGGTCGAGTTGTTAA (hom conf R)
                                   SEQ ID NO: 23
CAGCGCAGTCGCACGAATAT
```

The obtained transformed strain was named Cgl-TH-2.

2-3: Application of Mutation for Pyruvate Carboxylase (Pyc) Expression Enhancement For the purpose of improving L-threonine production through the oxaloacetate pool increase, the expression of the pyc gene corresponding to pyruvate carboxylase was to be increased. For the enhancement of pyc expression, the promoter of the pyc gene was replaced with the Pcj7 promoter. The fragment of the Pcj7 promoter was obtained via PCR using the pECCG117-Pcj7-GFP plasmid (Korean Patent No. 10-0620092) as a template along with the primers of SEQ ID NO: 24 and SEQ ID NO: 16.

```
(CJ7 F)
                                   SEQ ID NO: 24
CAACCTTTGCAAGGTGAAAAAGAAACATCCCAGCGCTACT (CJ7 R)
                                   SEQ ID NO: 16
TGTGTGAGTCGACATGAGTGTTTCCTTTCGTTGGG
```

The upstream region of the pyc promoter was obtained for homologous recombination for replacement of the Pcj7 promoter for the pyc promoter. Specifically, the fragment of the upstream region of the pyc promoter was obtained via PCR using the genomic DNA of *Corynebacterium glutamicum* 13032 as a template along with the primers of SEQ ID NO: 25 and SEQ ID NO: 26.

```
(upstream F)
                                   SEQ ID NO: 25
TCGAGCTCGGTACCCTGACAGTTGCTGATCTGGCT (upstream R)
                                   SEQ ID NO: 26
AGTAGCGCTGGGATGTTTCTTTTTCACCTTGCAAAGGTTG
```

In order to obtain the N-terminus of the coding sequence of pyc, which was to be utilized as a homologous region downstream of the Pcj7 promoter, PCR was performed using the genomic DNA of *Corynebacterium glutamicum* 13032 as a template along with the primers of SEQ ID NO: 25 and SEQ ID NO: 26, and the fragment downstream of the pyc promoter was obtained.

```
(pyc F)
                                   SEQ ID NO: 27
GGAATAATTACTCTAATGTCGACTCACACATCTTC (pyc R)
                                   SEQ ID NO: 28
CTCTAGAGGATCCCCGGCATTTTCAGACAGGAAGC
```

The three PCR fragments obtained via the above procedure and the vector pDZ for chromosomal transformation digested with SmaI restriction enzyme were cloned using the Gibson assembly method to thereby obtain a recombinant plasmid, which was named pDZ-Pcj7_pyc. The cloning was performed by mixing the Gibson assembly reagent and each of the gene fragments in a calculated number of moles, followed by preservation at 50° C. for 1 hour.

The constructed pDZ-Pcj7_pyc vector was transformed into the Cgl-TH-2 strain by electroporation and then subjected to secondary crossover to obtain a strain in which the wild-type pyc gene was replaced with the mutant Pcj7_pyc gene on the chromosome. The corresponding genetic manipulation was confirmed through genome sequencing and PCR using SEQ ID NO: 29 and SEQ ID NO: 30 capable of respectively amplifying the outside sites of the upstream and downstream regions of homologous recombination where the corresponding gene was inserted.

```
(pyc conf F)
                          SEQ ID NO: 29
ACGCACTCGGTGAAGGCGTG (pyc conf R)
                          SEQ ID NO: 30
CGCTTCAGCTTCACGAGATG
```

The obtained transformed strain was named Cgl-TH-3.

2-4: Insertion of One Copy of Protein (ThrA(S352P)BC) Having Mutant L-Threonine Operon, Ncgl0179 Deletion, and Bifunctional Aspartokinase/Homoserine Dehydrogenase 1

In order enhance L-threonine biosynthesis, the *E. coli*-derived L-threonine operon was to be applied. Especially, in the thrA gene having bifunctional aspartokinase/homoserine dehydrogenase 1, thrA(S352P) (*J Bacteriol.* 1993 February; 175(4):959-65) mutation was applied in order to cancel the feedback inhibition on L-threonine. In addition, the expression of the L-threonine operon was to be increased by using the SPL7 promoter (Korean Patent No. 10-1783170).

In order to insert the SPL7_thrA(S352P)BC in the Ncgl0179 position, the fragments of the homologous regions upstream and downstream of Ncgl0179 were subjected to nucleotide sequence amplification by using the genomic DNA of *Corynebacterium glutamicum* ATCC13032 as a template along with SEQ ID NOS: 31 and 32 and SEQ ID NOS: 37 and 38, respectively. In addition, SPL7 was amplified by using the synthesized SPL7 promoter as a template along with SEQ ID NO: 33 and SEQ ID NO: 34.

The upstream and downstream regions of the 352nd amino acid of thrA(S352P) were subjected to nucleotide sequence amplification using SEQ ID NOS: 35 and 36 and SEQ ID NOS: 39 and 40, respectively.

```
(Ncgl0179 UP F)
                          SEQ ID NO: 31
TCGAGCTCGGTACCCTTTTGAGTAATTGGTAATAC (Ncgl0179 UP R)
                          SEQ ID NO: 32
TGAAGCGCCGGTACCCGCTTAAACGGGCGATTAT (Ncgl0179 DOWN F)
                          SEQ ID NO: 37
ATGAATCATCAGTAATTAATGGCCCTCGATTTGGC (Ncgl0179 DOWN R)
                          SEQ ID NO: 38
TCTAGAGGATCCCCTGGAATAATCAGACTCTGGA (SPL7 F)
                          SEQ ID NO: 33
ATCGCCCGTTTAAGCGGGTACCGGCGCTTCATGT (SPL7 R)
                          SEQ ID NO: 34
CTTCAACACTCGCATGATATCTGTTTTGATCTCCT (S352P UP F)
                          SEQ ID NO: 35
ATCAAAACAGATATCATGCGAGTGTTGAAGTTCGG (S352P UP R)
                          SEQ ID NO: 36
TACTGTATTCGGAAGATGGTTGCGTAATCAGCACCAC
```

-continued

```
(S352P DOWN F)
                          SEQ ID NO: 39
GTGGTGCTGATTACGCAACCATCTTCCGAATACAGTA (S352P DOWN R)
                          SEQ ID NO: 40
AAATCGAGGGCCATTAATTACTGATGATTCATCATC
```

The five PCR fragments obtained via the above procedure and the vector pDZ for chromosomal transformation digested with SmaI restriction enzyme were cloned using the Gibson assembly method to thereby obtain a recombinant plasmid, which was named pDZ-SPL7_thrA(S352P)BC. The cloning was performed by mixing the Gibson assembly reagent and each of the gene fragments in a calculated number of moles, followed by preservation at 50° C. for 1 hour.

The prepared pDZ-SPL7_thrA(S352P)BC vector was transformed into the Cgl-TH-3 strain by electroporation and then subjected to secondary crossover to obtain a strain in which the SPL7_thrA(S352P)BC operon was inserted on the chromosome. The corresponding genetic manipulation was confirmed through genome sequencing and PCR using the primers of SEQ ID NO: 41 and SEQ ID NO: 42 capable of respectively amplifying the outside sites of the upstream and downstream regions of homologous recombination where the corresponding gene was inserted.

```
(thr conf F)
                          SEQ ID NO: 41
GATTCACATCACCAATGTC (thr conf R)
                          SEQ ID NO: 42
GACACCATCGCAGCCCGAC
```

The obtained transformed strain was named Cgl-TH-4.

The strain Cgl-TH-4 was named CJ09-5010. The strain was internationally deposited at the Korean Culture Center of Microorganisms (KCCM), an international depositary, on 31 May 2019, under the provisions of the Budapest Treaty, and assigned accession number KCCM12537P.

2-5: L-Threonine Production by Mutant L-Threonine Exporter (RhtC)-Introduced *Corynebacterium* Strain The pDZ-PgapA_rhtC, pDZ-PgapA_rhtC(m1), pDZ-PgapA_rhtC(m2), pDZ-PgapA_rhtC(m3), and pDZ-PgapA_rhtC(m4) vectors constructed in Example 1 were transformed into the Cgl-TH-4 strain by electroporation and then subjected to secondary crossover to obtain strains in which wild-type rhtC and four rhtC genes were inserted on the chromosome, respectively. The corresponding genetic manipulation was confirmed through genome sequencing and PCR using the primers of SEQ ID NO: 53 and SEQ ID NO: 54 capable of respectively amplifying the outside sites of the upstream and downstream regions of homologous recombination where the corresponding gene was inserted.

```
(HR outside F)
                          SEQ ID NO: 53
AAGGAATATCCCGGAGAACC (HR outside R)
                          SEQ ID NO: 54
TTGCGTTTGAAAAGCCCTCG
```

The obtained transformed strains were named Cgl-TH-5, Cgl-TH-5(m1), Cgl-TH-5(m2), Cgl-TH-5(m3), and Cgl-TH-5(m4), respectively.

Furthermore, in order to investigate the effect of mutant rhtC introduction in the *Corynebacterium* strain, the prepared Cgl-TH-5, Cgl-TH-5(m1), Cgl-TH-5(m2), Cgl-TH-5 (m3), and Cgl-TH-5(m4) strains were cultured via the following method to compare the amount of L-threonine production. Each strain was seeded in a 250 mL corner-baffle flask containing 25 mL of a seed medium (glucose 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100 μg, thiamine HCl 1,000 μg, calcium pantothenate 2000 μg, nicotinamide 2000 μg, pH 7.0 (based on 1 L of distilled water)) and cultured with shaking at 30° C. at 200 rpm for 20 hours. Then, 1 mL of the seed culture was inoculated into a 250 mL corner-baffle flask containing 25 mL of a production medium (glucose 30 g, $(NH_4)_2SO_4$ 15 g, $MgSO_4$ $7H_2O$ 1.2 g, $KH_2PO_4$ 1 g, yeast extract 5 g, biotin 900 μg, thiamine hydrochloride 4500 μg, calcium pantothenate 4500 μg, $CaCO_3$ 30 g, and pH 7.0 (based on 1 L of distilled water)) and cultured with shaking at 30° C. at 200 rpm for 24 hours. Upon completion of the culture, the amount of L-threonine production was measured via HPLC, and the results are shown in Table 3.

TABLE 3

| Strain name | Amount of L-threonine production (g/L) | L-Threonine yield (*100 g/g, %) |
|---|---|---|
| Cgl-TH-4 | 11.1 | 15.9 |
| Cgl-TH-5 | 14.0 | 20.0 |
| Cgl-TH-5(m1) | 17.9 | 25.6 |
| Cgl-TH-5(m2) | 24.0 | 34.3 |
| Cgl-TH-5(m3) | 21.8 | 31.1 |
| Cgl-TH-5(m4) | 17.9 | 25.6 |

As shown in Table 3, Cgl-TH-4, prepared by way of the method of Example 2-4, showed an L-threonine production result of 11.1 g/L, and Cgl-TH-5, into which the wild-type PgapA_rhtC trait was inserted, produced L-threonine at 14.0 g/L. In addition, Cgl-TH-5(m1), Cgl-TH-5(m2), Cgl-TH-5 (m3), and Cgl-TH-5(m4), into which the mutant PgapA_r-htC(m) traits were inserted, produced L-threonine at 17.9 g/L, 24.0 g/L, 21.8 g/L, and 17.9 g/L, respectively. As for the L-threonine fermentation yield, Cgl-TH-5 showed an increase of 4.1% p compared with Cgl-TH-4, whereas the Cgl-TH-5(m1), Cgl-TH-5(m2), Cgl-TH-5(m3), and Cgl-TH-5(m4) strains, to which the mutants were applied, showed increases of 9.7% p, 18.4% p, 15.3% p, and 9.7% p, respectively, compared with Cgl-TH-4. Especially, the increases in yield for Cgl-TH-5(m2) and Cgl-TH-5(m3) were about 4 times greater than that of Cgl-TH-5. The mutant RhtC applied to Cgl-TH-5(m2) had the amino acid sequence of SEQ ID NO: 94, and specifically included the mutation (L62S) in which leucine (Leu) was modified into serine (Ser) at the 62nd amino acid position. The mutant RhtC applied to Cgl-TH-5(m3) had the amino acid sequence of SEQ ID NO: 93, and specifically included the mutation (A53T) in which alanine (Ala) was modified into threonine (Thr) at the 53rd amino acid position.

The two strains Cgl-TH-5(m2) and Cgl-TH-5(m3) were named CA09-5012 and CA09-5036, respectively. These strains were internationally deposited at the Korean Culture Center of Microorganisms (KCCM), an international depositary, on 31 May 2019, under the provisions of the Budapest Treaty, and assigned accession numbers KCCM12538P and KCCM12539P, respectively.

Example 3: L-Threonine Production by Mutant L-Threonine Exporter-Introduced *E. coli* Strain The empty vector pCL1920, and pCL1920-Pn_rhtC prepared and four mutant plasmids selected in Example 1 were transformed into the *E. coli* strain TF4076 (KFCC10718, Korean Patent Application No. 90-22965) to prepare TF4076/pCL1920, TF4076/pCL1920-Pn_rhtC, TF4076/pCL1920-Pn_rhtC(m1), TF4076/pCL1920-Pn_rhtC(m2), TF4076/pCL1920-Pn_rhtC(m3), and TF4076/pCL1920-Pn_rhtC(m4), respectively. For comparison of the amount of L-threonine production among the prepared strains, flask evaluation was performed. As for the flask test, each of the strains was streaked on an LB plate containing 50 μg/mL chloramphenicol and cultured in an incubator at 33° C. for 16 hours. Thereafter, a single colony was inoculated in 2 mL of LB medium, and then cultured in an incubator at 200 rpm/33° C. for 12 hours. In addition, 25 mL of a threonine-producing flask medium having a composition shown in Table 4 below was placed in a 250 mL flask, and 500 μL of the culture obtained via the previous culture was added thereto. Thereafter, the flask was incubated in an incubator at 200 rpm/33° C. for 48 hours, and then the amount of threonine obtained from each strain was compared by HPLC, and the results are shown in Table 5 below.

TABLE 4

| Composition | Content (per liter) |
|---|---|
| Glucose | 70 g |
| Ammonium sulfate | 25 g |
| $KH_2PO_4$ | 1 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |
| Methionine | 0.15 g |
| pH | 6.8 |

TABLE 5

| Strain name | Amount of L-threonine production (g/L) | L-Threonine yield (*100 g/g, %) |
|---|---|---|
| TF4076 | 25.7 | 36.7 |
| TF4076/pCL1920 | 25.9 | 37.0 |
| TF4076/pCL1920-Pn_rhtC | 29.9 | 42.6 |
| TF4076/pCL1920-Pn_rhtC(m1) | 33.4 | 47.7 |
| TF4076/pCL1920-Pn_rhtC(m2) | 40.4 | 57.7 |
| TF4076/pCL1920-Pn_rhtC(m3) | 38.8 | 55.4 |
| TF4076/pCL1920-Pn_rhtC(m4) | 33.8 | 48.3 |

As shown in Table 5, the introduction of the mutant rhtC plasmids into the *E. coli* strain having L-threonine producing ability resulted in a great increase in L-threonine yield. In particular, the application of pCL1920-Pn_rhtC(m2) and pCL1920-Pn_rhtC(m3) showed great increases in L-threonine yield.

Example 4: Saturated Mutagenesis of 62nd Amino Acid Leucine of L-Threonine Exporter Since the mutant rhtC(L62S) showed a high yield increase effect compared with the wild type as described in Tables 3 and 5, the improvement validity of L-threonine export of the 62nd position was to be validated by mutating the 62nd amino acid leucine into another amino acid in RhtC. In order to mutate leucine into 19 amino acids other than leucine, site-directed mutagenesis was performed via the following method using the pDZ-PgapA-rhtC prepared in Example 1 as a template.

TABLE 6

| Composition | Content (μL) |
| --- | --- |
| 10X pfu-X Buffer | 5 |
| 10 mM dNTP Mix | 1 |
| pfu-X Polymerase | 1 |
| Mutagenic forward primer (5 pmol) | 2 |
| Mutagenic reverse primer (5 pmol) | 2 |
| pDZ-PgapA_rhtC (template DNA, 200 ng/μL) | 1 |
| dH$_2$O | 38 |
| Total | 50 |

TABLE 7

| Number of cycles | Temperature | Time |
| --- | --- | --- |
| 1 | 95° C. | 5 min |
| 18 | 95° C. | 30 sec |
| | 60° C. | 1 min |
| | 68° C. | 10 min |

For the substitution of the 62nd amino acid leucine (L) with another amino acid in RhtC, the composition as show in Table 6 was prepared, and PCR was performed according to the conditions of Table 7. In PCR, each mutagenic primer set in Table 8 was used. After completion of PCR, 1 μL of DpnI restriction enzyme was added, followed by incubation at 37° C. for one hour. Mutant pDZ-PgapA_rhtC plasmids were obtained by transforming 3 μL of DNA treated with DpnI into DH5a competent cells, and each of the mutations shown in Table 8 was confirmed by sequencing.

TABLE 8

| Mutant rhtC plasmid | SEQ ID NO | Nucleotide sequence |
| --- | --- | --- |
| pDZ-PgapA_rhtC L62R | SEQ ID NO: 57 | GCGCTGCTTGGCCTGCATCGTATT ATCGAAAAAATGGCC |
| | SEQ ID NO: 58 | GGCCATTTTTTCGATAATACGATG CAGGCCAAGCAGCGC |
| pDZ-PgapA_rhtC L62A | SEQ ID NO: 59 | GCGCTGCTTGGCCTGCATGCGATT ATCGAAAAAATGGCC |
| | SEQ ID NO: 60 | GGCCATTTTTTCGATAATCGCATG CAGGCCAAGCAGCGC |
| pDZ-PgapA_rhtC L62D | SEQ ID NO: 61 | GCGCTGCTTGGCCTGCATGACATT ATCGAAAAAATGGCC |
| | SEQ ID NO: 62 | GGCCATTTTTTCGATAATGTCATG CAGGCCAAGCAGCGC |
| pDZ-PgapA_rhtC L62K | SEQ ID NO: 63 | GCGCTGCTTGGCCTGCATAAAATT ATCGAAAAAATGGCC |
| | SEQ ID NO: 64 | GGCCATTTTTTCGATAATTTTATG CAGGCCAAGCAGCGC |
| pDZ-PgapA_rhtC L62P | SEQ ID NO: 65 | GCGCTGCTTGGCCTGCATCCGATT ATCGAAAAAATGGCC |
| | SEQ ID NO: 66 | GGCCATTTTTTCGATAATCGGATG CAGGCCAAGCAGCGC |

TABLE 8-continued

| Mutant rhtC plasmid | SEQ ID NO | Nucleotide sequence |
| --- | --- | --- |
| pDZ-PgapA_rhtC L62C | SEQ ID NO: 67 | GCGCTGCTTGGCCTGCATTGCATT ATCGAAAAAATGGCC |
| | SEQ ID NO: 68 | GGCCATTTTTTCGATAATGCAATG CAGGCCAAGCAGCGC |
| pDZ-PgapA_rhtC L62G | SEQ ID NO: 69 | GCGCTGCTTGGCCTGCATGGCATT ATCGAAAAAATGGCC |
| | SEQ ID NO: 70 | GGCCATTTTTTCGATAATGCCATG CAGGCCAAGCAGCGC |
| pDZ-PgapA_rhtC L62T | SEQ ID NO: 71 | GCGCTGCTTGGCCTGCATACGATT ATCGAAAAAATGGCC |
| | SEQ ID NO: 72 | GGCCATTTTTTCGATAATCGTATG CAGGCCAAGCAGCGC |
| pDZ-PgapA_rhtC L62I | SEQ ID NO: 73 | GCGCTGCTTGGCCTGCATATTATT ATCGAAAAAATGGCC |
| | SEQ ID NO: 74 | GGCCATTTTTTCGATAATAATATG CAGGCCAAGCAGCGC |
| pDZ-PgapA_rhtC L62Y | SEQ ID NO: 75 | GCGCTGCTTGGCCTGCATTATATT ATCGAAAAAATGGCC |
| | SEQ ID NO: 76 | GGCCATTTTTTCGATAATATAATG CAGGCCAAGCAGCGC |
| pDZ-PgapA_rhtC L62V | SEQ ID NO: 77 | GCGCTGCTTGGCCTGCATGTGATT ATCGAAAAAATGGCC |
| | SEQ ID NO: 78 | GGCCATTTTTTCGATAATCACATG CAGGCCAAGCAGCGC |
| pDZ-PgapA_rhtC L62H | SEQ ID NO: 79 | GCGCTGCTTGGCCTGCATCATATT ATCGAAAAAATGGCC |
| | SEQ ID NO: 80 | GGCCATTTTTTCGATAATATGATG CAGGCCAAGCAGCGC |
| pDZ-PgapA_rhtC L62F | SEQ ID NO: 81 | GCGCTGCTTGGCCTGCATTTCATT ATCGAAAAAATGGCC |
| | SEQ ID NO: 82 | GGCCATTTTTTCGATAATGAAATG CAGGCCAAGCAGCGC |
| pDZ-PgapA_rhtC L62M | SEQ ID NO: 83 | GCGCTGCTTGGCCTGCATATGATT ATCGAAAAAATGGCC |
| | SEQ ID NO: 84 | GGCCATTTTTTCGATAATCATATG CAGGCCAAGCAGCGC |
| pDZ-PgapA_rhtC L62Q | SEQ ID NO: 85 | GCGCTGCTTGGCCTGCATCAGATT ATCGAAAAAATGGCC |
| | SEQ ID NO: 86 | GGCCATTTTTTCGATAATCTGATG CAGGCCAAGCAGCGC |
| pDZ-PgapA_rhtC L62N | SEQ ID NO: 87 | GCGCTGCTTGGCCTGCATAACATT ATCGAAAAAATGGCC |
| | SEQ ID NO: 88 | GGCCATTTTTTCGATAATGTTATG CAGGCCAAGCAGCGC |
| pDZ-PgapA_rhtC L62E | SEQ ID NO: 89 | GCGCTGCTTGGCCTGCATGAAATT ATCGAAAAAATGGCC |
| | SEQ ID NO: 90 | GGCCATTTTTTCGATAATTTCATG CAGGCCAAGCAGCGC |
| pDZ-PgapA_rhtC L62W | SEQ ID NO: 91 | GCGCTGCTTGGCCTGCATTGGATT ATCGAAAAAATGGCC |
| | SEQ ID NO: 92 | GGCCATTTTTTCGATAATCCAATG CAGGCCAAGCAGCGC |

The pDZ-PgapA_rhtC L62R, pDZ-PgapA_rhtC L62A, pDZ-PgapA_rhtC L62D, pDZ-PgapA_rhtC L62K, pDZ-PgapA_rhtC L62P, pDZ-PgapA_rhtC L62C, pDZ-PgapA_r-htC L62G, pDZ-PgapA_rhtC L62T, pDZ-PgapA_rhtC L62I, pDZ-PgapA_rhtC L62Y, pDZ-PgapA_rhtC L62V, pDZ-PgapA_rhtC L62H, pDZ-PgapA_rhtC L62F, pDZ-PgapA_rhtC L62M, pDZ-PgapA_rhtC L62Q, pDZ-PgapA_rhtC L62N, pDZ-PgapA_rhtC L62E, and pDZ-PgapA_rhtC L62W vectors constructed as shown in Table 8 were transformed into the Cgl-TH-4 strain by the method in Example 2-5 through electroporation, and then subjected to secondary crossover to obtain 19 species of strains in which the mutant rhtC genes were inserted on the chromosome, respectively. The corresponding genetic manipulation was confirmed through genome sequencing and PCR using the primers of SEQ ID NO: 53 and SEQ ID NO: 54 capable of respectively amplifying the outside sites of the upstream and downstream regions of homologous recombination where the corresponding gene was inserted.

```
(HR outside F)
                                    SEQ ID NO: 53
AAGGAATATCCCGGAGAACC (HR outside R)
                                    SEQ ID NO: 54
TTGCGTTTGAAAAGCCCTCG
```

The obtained transformed strains were named Cgl-TH-5 (L62R), Cgl-TH-5(L62A), Cgl-TH-5(L62D), Cgl-TH-5 (L62K), Cgl-TH-5(L62P), Cgl-TH-5(L62C), Cgl-TH-5 (L62G), Cgl-TH-5(L62T), Cgl-TH-5(L62I), Cgl-TH-5 (L62Y), Cgl-TH-5(L62V), Cgl-TH-5(L62H), Cgl-TH-5 (L62F), Cgl-TH-5(L62M), Cgl-TH-5(L62Q), Cgl-TH-5 (L62N), Cgl-TH-5(L62E), and Cgl-TH-5(L62W), respectively.

The 18 species of strains prepared by the above method and the previously prepared Cgl-TH-4, Cgl-TH-5, and Cgl-TH-5(m2) strains were cultured using the L-threonine producing flask media and the culture method in Example 2-5. After completion of the culture, the amount of L-threonine production was measured via HPLC, and the results are shown in Table 9.

TABLE 9

| Strain name | rhtC form | Amount of L-threonine production (g/L) | L-Threonine yield (g/g, %) | Yield improvement compared with wild type (Δ, % p) |
|---|---|---|---|---|
| Cgl-TH-4 | — | 11.3 | 16.1 | — |
| Cgl-TH-5 | rhtC wild type | 14.0 | 20.0 | — |
| Cgl-TH-5(m2) | rhtC L62S | 24.0 | 34.3 | 14.3 |
| Cgl-TH-5(L62R) | rhtC L62R | 24.9 | 35.6 | 15.6 |
| Cgl-TH-5(L62A) | rhtC L62A | 23.5 | 33.5 | 13.5 |
| Cgl-TH-5(L62D) | rhtC L62D | 17.5 | 24.9 | 4.9 |
| Cgl-TH-5(L62K) | rhtC L62K | 24.0 | 34.3 | 14.3 |
| Cgl-TH-5(L62P) | rhtC L62P | 23.3 | 33.2 | 13.2 |
| Cgl-TH-5(L62C) | rhtC L62C | 15.8 | 22.6 | 2.6 |
| Cgl-TH-5(L62G) | rhtC L62G | 19.8 | 28.3 | 8.3 |
| Cgl-TH-5(L62T) | rhtC L62T | 25.8 | 36.9 | 16.9 |
| Cgl-TH-5(L62I) | rhtC L62I | 17.5 | 24.9 | 4.9 |
| Cgl-TH-5(L62Y) | rhtC L62Y | 16.4 | 23.4 | 3.4 |
| Cgl-TH-5(L62V) | rhtC L62V | 22.5 | 32.2 | 12.2 |
| Cgl-TH-5(L62H) | rhtC L62H | 23.8 | 34.0 | 14.0 |
| Cgl-TH-5(L62F) | rhtC L62F | 16.5 | 23.6 | 3.6 |
| Cgl-TH-5(L62M) | rhtC L62M | 19.1 | 27.3 | 7.3 |
| Cgl-TH-5(L62Q) | rhtC L62Q | 20.0 | 28.6 | 8.6 |
| Cgl-TH-5(L62N) | rhtC L62N | 21.8 | 31.2 | 11.2 |
| Cgl-TH-5(L62E) | rhtC L62E | 18.2 | 26.0 | 6.0 |
| Cgl-TH-5(L62W) | rhtC L62W | 20.7 | 29.6 | 9.6 |

As shown in Table 9, all of the 19 species of mutants, to which the mutation of the 62nd amino acid in the RhtC protein was applied, showed a fermentation yield improvement of 3.4-16.9% p relative to Cgl-TH-5 into which wild-type rhtC was inserted.

Example 5: AHV-Resistant Strain Screening Through Artificial Mutation

The resistance to 2-amino-3-hydroxy-valerate (AHV), which is an L-threonine analog, was imparted to *Corynebacterium glutamicum* KFCC10881 (Korean Patent No. 0159812) as a parent strain.

Mutation was induced by artificial mutation using N-methyl-N'-nitro-N-nitrosoguanidine (NTG). The KFCC10881 strain cultured in the seed medium in Example 2-5 for 18 hours was again inoculated into 4 mL of the seed medium, and then cultured until $OD_{660}$ reached about 1.0. The culture was centrifuged to recover the cells, and then the cells were washed twice with 50 mM Tris-malate buffer (pH 6.5) and suspended in the final 4 mL of the same buffer. An NTG solution (2 mg/mL in 0.05 M Tris-malate buffer (pH 6.5)) was added to the cell suspension to have a final concentration of 150 mg/L, and then allowed to stand at room temperature for 20 minutes. Thereafter, the cells were recovered by centrifugation and washed twice with the same buffer to remove the NTG. The finally washed cells were suspended in 4 mL of a 20% glycerol solution and then stored at −70° C. before use. The NTG-treated strains were plated on a minimal medium containing 3 g/L of AHV, and then 155 mutant KFCC10881 strains having AHV resistance were obtained through the above procedure.

Example 6: Selection of L-Threonine-Producing Strains from AHV-Resistant KFCC10881 Strains An L-threonine producing ability test was performed on the 155 AHV-resistant strains obtained in Example 5. The 155 strains each were inoculated into a 250 mL corner-baffle flask containing 25 mL of the seed medium in Example 2-5, and then cultured with shaking at 30° C. at 200 rpm for 20 hours. After 1 mL of the seed culture was inoculated into a 250 mL corner-baffle flask containing 24 mL of the L-threonine production medium (glucose 30 g, $KH_2PO_4$ 2 g, urea 3 g, $(NH_4)_2SO_4$ 40 g, peptone 2.5 g, CSL (Sigma) 5 g (10 mL), $MgSO_4$ $7H_2O$ 0.5 g, leucine 400 mg, $CaCO_3$ 20 g, pH 7.2 (based on 1 L of distilled water)) and then cultured with shaking at 30° C. at 200 rpm for 48 hours.

After completion of the culture, the amounts of several amino acids produced were measured using HPLC. The concentrations of the amino acids in the cultures for the top 22 strains, which were shown to have excellent L-threonine producing ability, among the 155 strains experimented on, are shown in Table 10. The 22 candidate strains confirmed through the above procedure were named KFCC10881-1 to KFCC10881-22.

TABLE 10

| Strain name | OD | L-Threonine (g/L) | Homoserine (g/L) |
|---|---|---|---|
| KFCC10881 | 58.5 | 0.0 | 0.1 |
| KFCC10881-1 | 60.1 | 2.0 | 1.5 |
| KFCC10881-2 | 57.1 | 3.0 | 2.2 |
| KFCC10881-3 | 47.3 | 2.8 | 2.3 |
| KFCC10881-4 | 51.7 | 3.2 | 2.1 |
| KFCC10881-5 | 58.4 | 3.1 | 2.2 |
| KFCC10881-6 | 52.6 | 3.4 | 2.5 |
| KFCC10881-7 | 14.2 | 0.4 | 0.2 |
| KFCC10881-8 | 55.8 | 3.0 | 2.0 |
| KFCC10881-9 | 44.3 | 3.2 | 2.8 |
| KFCC10881-10 | 47.5 | 3.7 | 3.0 |
| KFCC10881-11 | 57.0 | 2.7 | 1.8 |
| KFCC10881-12 | 51.8 | 3.3 | 3.5 |

TABLE 10-continued

| Strain name | OD | L-Threonine (g/L) | Homoserine (g/L) |
|---|---|---|---|
| KFCC10881-13 | 49.8 | 3.0 | 2.3 |
| KFCC10881-14 | 62.7 | 2.4 | 2.1 |
| KFCC10881-15 | 62.4 | 2.9 | 2.7 |
| KFCC10881-16 | 59.6 | 2.8 | 2.5 |
| KFCC10881-17 | 24.1 | 0.1 | 0.2 |
| KFCC10881-18 | 60.5 | 2.6 | 2.5 |
| KFCC10881-19 | 60.0 | 3.0 | 1.9 |
| KFCC10881-20 | 65.8 | 2.7 | 2.0 |
| KFCC10881-21 | 17.3 | 0.3 | 0.3 |
| KFCC10881-22 | 60.1 | 3.5 | 1.9 |

As shown in Table 10, 22 species of strains having AHV resistance showed the L-threonine production results, which were not observed in the control group (KFCC10881). Among the AHV-resistant strains, KFCC10881-10 was selected as the best L-threonine-producing strain.

Example 7: L-Threonine Production by Mutant L-Threonine Exporter-Introduced KFCC10881-10 Strains The pDZ-PgapA_rhtC, pDZ-PgapA_rhtC(m2), and pDZ-PgapA_rhtC(m3) vectors constructed in Example 1 and the pDZ-PgapA_rhtC L62R, pDZ-PgapA_rhtC L62A, pDZ-PgapA_rhtC L62D, pDZ-PgapA_rhtC L62K, pDZ-PgapA_rhtC L62P, pDZ-PgapA_rhtC L62C, pDZ-PgapA_rhtC L62G, pDZ-PgapA_rhtC L62T, pDZ-PgapA_rhtC L62I, pDZ-PgapA_rhtC L62Y, pDZ-PgapA_rhtC L62V, pDZ-PgapA_rhtC L62H, pDZ-PgapA_rhtC L62F, pDZ-PgapA_rhtC L62M, pDZ-PgapA_rhtC L62Q, pDZ-PgapA_rhtC L62N, pDZ-PgapA_rhtC L62E, pDZ-PgapA_rhtC L62W vectors constructed as shown in Table in Example 4 were transformed into the KFCC10881-10 strain by electroporation and then subjected to secondary crossover to obtain 22 species of strains in which the mutant rhtC genes were inserted on the chromosome, respectively. The corresponding genetic manipulation was confirmed through genome sequencing and PCR using the primers of SEQ ID NO: 53 and SEQ ID NO: 54 capable of respectively amplifying the outside sites of the upstream and downstream regions of homologous recombination where the corresponding gene was inserted.

```
(HR outside F)
                          SEQ ID NO: 53
AAGGAATATCCCGGAGAACC (HR outside R)
                          SEQ ID NO: 54
TTGCGTTTGAAAAGCCCTCG
```

The obtained transformed strains were named KFCC10881-10(rhtC WT), KFCC10881-10(rhtC L62S), KFCC10881-10(rhtC A53T), KFCC10881-10(rhtC L62R), KFCC10881-10(rhtC L62A), KFCC10881-10(rhtC L62D), KFCC10881-10(rhtC L62K), KFCC10881-10(rhtC L62P), KFCC10881-10(rhtC L62C), KFCC10881-10(rhtC L62G), KFCC10881-10(rhtC L62T), KFCC10881-10(rhtC L62I), KFCC10881-10(rhtC L62Y), KFCC10881-10(rhtC L62V), KFCC10881-10(rhtC L62H), KFCC10881-10(rhtC L62F), KFCC10881-10(rhtC L62M), KFCC10881-10(rhtC L62Q), KFCC10881-10(rhtC L62N), KFCC10881-10(rhtC L62E), and KFCC10881-10(rhtC L62W), respectively.

The corresponding genetic manipulation was confirmed through genome sequencing and PCR using the primers of SEQ ID NO: 53 and SEQ ID NO: 54, which were capable of respectively amplifying the outside sites of the upstream and downstream regions of homologous recombination where the corresponding genes were inserted.

The 22 species of strains prepared by the above method were cultured using the L-threonine production medium and the culture method in Example 6. After completion of the culture, the amount of L-threonine production was measured via HPLC, and the results are shown in Table 11.

TABLE 11

| Strain name | Amount of L-threonine production (g/L) | L-Threonine yield (g/g, %) | Yield improvement compared with wild-type rhtC (Δ, % p) |
|---|---|---|---|
| KFCC10881-10 | 3.8 | 12.7 | — |
| KFCC10881-10(rhtC WT) | 5.5 | 18.3 | — |
| KFCC10881-10(rhtC A53T) | 9.0 | 30.0 | 11.7 |
| KFCC10881-10(rhtC L62S) | 10.1 | 33.5 | 15.2 |
| KFCC10881-10(rhtC L62R) | 10.0 | 33.2 | 14.9 |
| KFCC10881-10(rhtC L62A) | 9.8 | 32.5 | 14.2 |
| KFCC10881-10(rhtC L62D) | 6.6 | 22.1 | 3.8 |
| KFCC10881-10(rhtC L62K) | 10.2 | 34.1 | 15.8 |
| KFCC10881-10(rhtC L62P) | 10.0 | 33.2 | 14.9 |
| KFCC10881-10(rhtC L62C) | 5.9 | 19.8 | 1.5 |
| KFCC10881-10(rhtC L62G) | 7.8 | 26.1 | 7.8 |
| KFCC10881-10(rhtC L62T) | 10.2 | 34.0 | 15.7 |
| KFCC10881-10(rhtC L62I) | 6.3 | 20.9 | 2.6 |
| KFCC10881-10(rhtC L62Y) | 6.8 | 22.5 | 4.2 |
| KFCC10881-10(rhtC L62V) | 9.2 | 30.5 | 12.2 |
| KFCC10881-10(rhtC L62H) | 9.8 | 32.8 | 14.5 |
| KFCC10881-10(rhtC L62F) | 6.4 | 21.3 | 3.0 |
| KFCC10881-10(rhtC L62M) | 7.3 | 24.2 | 5.9 |
| KFCC10881-10(rhtC L62Q) | 7.9 | 26.3 | 8.0 |
| KFCC10881-10(rhtC L62N) | 8.9 | 29.5 | 11.2 |
| KFCC10881-10(rhtC L62E) | 7.4 | 24.5 | 6.2 |
| KFCC10881-10(rhtC L62W) | 8.5 | 28.2 | 9.9 |

As shown in Table 11, a high level of yield increase could be observed in the introduction of the mutant RhtC into KFCC10881-10 compared with wild-type RhtC, as in the results shown in Examples 3 and 4.

Example 8: L-Threonine Production by Mutant L-Threonine Exporter-Introduced TF4076 Strains The mutation of the present disclosure was introduced into other strain-derived rhtC having high homology with *E. coli* W3110-derived rhtC protein (SEQ ID NO: 1) to investigate the L-threonine production results.

Specifically, nucleotide sequence fragments (eco rhtC, sfe rhtC, efe rhtC) were secured from genomic DNA of *E. coli* W3110, *Shigella flexneri*, and *Escherichia fergusonii* by performing PCR, respectively, and each mutant rhtC, into which the L62S mutation was introduced, was prepared by way of the method of Example 1. The prepared mutant rhtC or wild-type rhtC of each strain was cloned to pCL1920 to secure the recombinant plasmids pCL1920-Pn_rhtC.eco, pCL1920-Pn_rhtC.eco L62S, pCL1920-Pn_rhtC.sfe, pCL1920-Pn_rhtC.sfe L62S, pCL1920-Pn_rhtC.efe, and pCL1920-Pn_rhtC.efe L62S.

The recombinant plasmids constructed as above were transformed into TF4076, which is an *E. coli* strain having L-threonine producing ability, and thereby TF4076/pCL1920, TF4076/pCL1920-Pn_rhtC.eco, TF4076/pCL1920-Pn_rhtC.eco L62S, TF4076/pCL1920-Pn_rhtC.sfe, TF4076/pCL1920-Pn_rhtC.sfe L62S, TF4076/pCL1920-Pn_rhtC.efe, and TF4076/pCL1920-Pn_rhtC.efe L62S strains were prepared. For comparison of the amount of L-threonine production among the prepared strains, flask evaluation was performed, and the results are shown in Table 12.

TABLE 12

| Strain name | Amount of L-threonine production (g/L) | L-Threonine yield (*100 g/g, %) |
|---|---|---|
| TF4076 | 25.7 | 36.7 |
| TF4076/pCL1920 | 25.9 | 37 |
| TF4076/pCL1920-Pn_rhtC.eco | 29.9 | 42.6 |
| TF4076/pCL1920-Pn_rhtC.eco L62S | 40.4 | 57.7 |
| TF4076/pCL1920-Pn_rhtC.sfe | 31.1 | 44.43 |
| TF4076/pCL1920-Pn_rhtC.sfe L62S | 41.5 | 59.29 |
| TF4076/pCL1920-Pn_rhtC.efe | 29.1 | 41.57 |
| TF4076/pCL1920-Pn_rhtC.efe L62S | 38.2 | 54.57 |

When mutant RhtC obtained by introducing the L62S mutation into RhtC derived from *E. coli* W3110, *Shigella flexneri*, and *Escherichia fergusonii* was introduced into TF4076, a higher level of yield increase compared with the wild-type RhtC, as in the results shown in Examples 3, 4, and 7.

It can therefore be seen that even though the reference sequence is varied, a substitution with another amino acid at a position corresponding to the 53rd or 62nd position of the present disclosure could improve L-threonine exporting ability.

From the above description, a person skilled in the art to which the present disclosure pertains will be able to understand that the present disclosure may be embodied in other specific forms without departing from the technical spirit or essential characteristics thereof. Therefore, the embodiments described above should be construed as exemplifying and not limiting the present disclosure. The scope of the present disclosure should be understood as embracing all changes or modifications derived from the definitions and scopes of the claims and their equivalents.

The invention claimed is:

1. An L-threonine exporter protein variant having comprising an amino acid sequence having at least 80% sequence identity to the amino acid sequence of SEQ ID NO: 1, wherein:

the amino acid sequence has a threonine at a position corresponding to the $53^{rd}$ position with respect to the amino acid sequence of SEQ ID NO: 1; or the amino acid sequence has any amino acid except for leucine at a position corresponding to the $62^{nd}$ position with respect to the amino acid sequence of SEQ ID NO: 1, and the L-threonine exporter protein variant has L-threonine exporting activity.

2. The L-threonine exporter protein variant of claim 1, wherein the any amino acid corresponding to the $62^{nd}$ position is selected from serine, arginine, alanine, aspartic acid, lysine, proline, cysteine, glycine, threonine, isoleucine, tyrosine, valine, histidine, phenylalanine, methionine, glutamine, asparagine, glutamic acid, or tryptophan.

3. The L-threonine exporter protein variant of claim 1, wherein the L-threonine exporter protein variant comprises an amino acid sequence of any one selected from the amino acid sequence of SEQ ID NOS: 93 to 112.

4. A polynucleotide encoding the L-threonine exporter protein variant of claim 1.

5. A vector comprising the polynucleotide of claim 4.

6. A microorganism capable of producing L-threonine, the microorganism comprising the L-threonine exporter protein variant of claim 1, a polynucleotide encoding the L-threonine exporter protein variant, or a vector comprising the polynucleotide encoding the L-threonine exporter variant.

7. The microorganism of claim 6, wherein the microorganism is a microorganism of *Corynebacterium* sp. or *Escherichia* sp.

8. A method for producing L-threonine, the method comprising culturing, in a medium, the microorganism of claim 6.

9. The method of claim 8, wherein the method further comprises recovering L-threonine from the cultured medium or microorganism.

* * * * *